US007989607B2

(12) United States Patent
Barbour et al.

(10) Patent No.: US 7,989,607 B2
(45) Date of Patent: Aug. 2, 2011

(54) CORN EVENT TC1507 AND METHODS FOR DETECTION THEREOF

(75) Inventors: Eric Barbour, Johnston, IA (US); James Wayne Bing, Ankeny, IA (US); Guy A. Cardineau, Tempe, AZ (US); Robert F. Cressman, Jr., Wilmington, DE (US); Manju Gupta, Carmel, IN (US); Mary E. Hartnett Locke, Mickleton, NJ (US); David Hondred, Altoona, IA (US); Joseph W. Keaschall, Clive, IA (US); Michael G. Koziel, Raleigh, NC (US); Terry EuClaire Meyer, Urbandale, IA (US); Daniel Moellenbeck, Granger, IA (US); Kenneth Edwin Narva, Zionsville, IN (US); Wilas Nirunsuksiri, Auburn, WA (US); Steven W. Ritchie, Omaha, NE (US); Marjorie L. Rudert, Boone, IA (US); Craig D. Sanders, Bear, DE (US); Aihua Shao, Johnston, IA (US); Steven Jeffrey Stelman, San Diego, CA (US); David S. Stucker, Johnston, IA (US); Laura Ann Tagliani, Zionsville, IN (US); William M. Van Zante, Urbandale, IA (US)

(73) Assignees: Pioneer Hi-Bred International, Inc., Johnston, IA (US); E. I. du Pont de Nemours and Company, Wilmington, DE (US); Dow Agrosciences LLC, Indianapolis, IN (US)

( * ) Notice: Subject to any disclaimer, the term of this patent is extended or adjusted under 35 U.S.C. 154(b) by 21 days.

(21) Appl. No.: 12/333,044

(22) Filed: Mar. 13, 2009

(65) Prior Publication Data

US 2009/0170109 A1 Jul. 2, 2009

Related U.S. Application Data

(60) Continuation of application No. 11/774,236, filed on Jul. 6, 2007, now Pat. No. 7,514,544, which is a division of application No. 10/837,105, filed on Apr. 30, 2004, now Pat. No. 7,288,643.

(60) Provisional application No. 60/467,772, filed on May 2, 2003.

(51) Int. Cl.
*C07H 21/02* (2006.01)
(52) U.S. Cl. ..................... 536/23.1; 435/975
(58) Field of Classification Search .................. None
See application file for complete search history.

(56) References Cited

U.S. PATENT DOCUMENTS

| 5,474,796 | A | 12/1995 | Brennan |
| 6,646,184 | B2 | 11/2003 | Hohn et al. |
| 6,713,259 | B2 | 3/2004 | Levine |
| 6,825,400 | B2 | 11/2004 | Behr et al. |
| 2001/0053519 | A1* | 12/2001 | Fodor et al. ............ 435/6 |

FOREIGN PATENT DOCUMENTS

WO WO 2004/011601 2/2004

OTHER PUBLICATIONS

New England Biolabs 1998/99 Catalog (NEB Catalog).*
Stratagene ("Gene Characterization Kits" 1988).*
Anonymous: "DAS-01507-1 (TC 1507)", Internet Article, Online Oct. 17, 2002, XP002312770, Internet: http://www.aqbios.com/dbase.php?acton=showprod&data=TC1507&frmat=long> 'retrieved on Jan. 4, 2005.
Anonymous: "Skov—og Naturstyrelsen" Internet Article, Online Dec. 11, 2000, XP002312769 Denmark, Internet: http://www.sns.dk//erhvogadm/hoeringer/n n1 00 10/indhold.htm> retried on Jan. 6, 2005.
Database EMBL 'Online! Nov. 18, 2002, "Mus musculus chromosome 5 clone rp23-426e16 strain C57BL/6J, complete sequence." XP 002312771, retried from EBI, Database accession No. AC084071.
Printout from http://www.aqbios.com/docroot/decdocs/04-225-004.pdf.
Printout from http://www.epa.gov/fedrgstr/EPA-IMPACT/2001/August/Day-14/20307.htm.
Printout from http://www.aqbios.com/docroot/decdocs/02122001/pdf.
New England Biolabs 1988/99 Catalog (NEB Catalog).

* cited by examiner

Primary Examiner — Christopher M. Babic
(74) Attorney, Agent, or Firm — Alston & Bird LLP

(57) ABSTRACT

The invention provides DNA compositions that relate to transgenic insect resistant maize plants. Also provided are assays for detecting the presence of the maize TC1507 event based on the DNA sequence of the recombinant construct inserted into the maize genome and the DNA sequences flanking the insertion site. Kits and conditions useful in conducting the assays are provided.

1 Claim, 1 Drawing Sheet

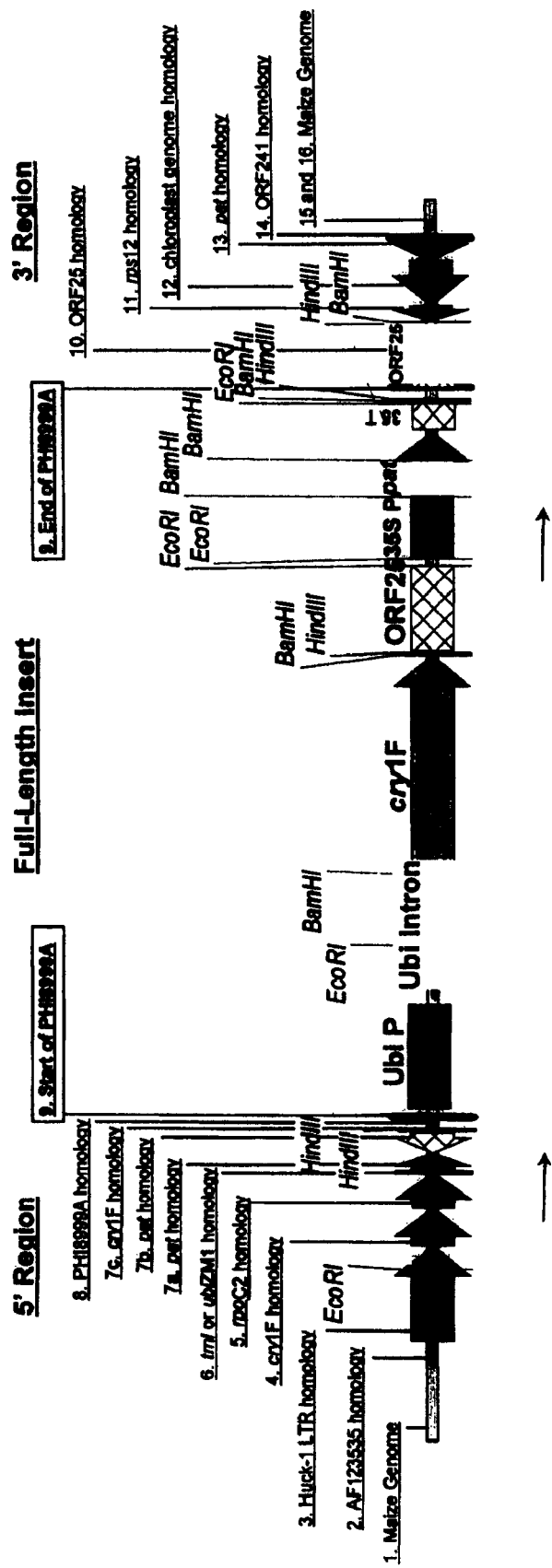

SEQUENCE LISTING

```
<160> NUMBER OF SEQ ID NOS: 57

<210> SEQ ID NO 1
<211> LENGTH: 30
<212> TYPE: DNA
<213> ORGANISM: Artificial Sequence
<220> FEATURE:
<223> OTHER INFORMATION: Event specific primer sequence designed for
      TC1507

<400> SEQUENCE: 1
gtagtactat agattatatt attcgtagag                                         30

<210> SEQ ID NO 2
<211> LENGTH: 30
<212> TYPE: DNA
<213> ORGANISM: Artificial Sequence
<220> FEATURE:
<223> OTHER INFORMATION: Event specific primer sequence designed for
      TC1507

<400> SEQUENCE: 2
gccatacaga actcaaaatc ttttccggag                                         30

<210> SEQ ID NO 3
<211> LENGTH: 25
<212> TYPE: DNA
<213> ORGANISM: Artificial Sequence
<220> FEATURE:
<223> OTHER INFORMATION: Event specific primer sequence designed for
      TC1507

<400> SEQUENCE: 3
```
tgtggtgttt gtggctctgt cctaa        25

<210> SEQ ID NO 4
<211> LENGTH: 25
<212> TYPE: DNA
<213> ORGANISM: Artificial Sequence
<220> FEATURE:
<223> OTHER INFORMATION: Event specific primer for TC1507

<400> SEQUENCE: 4 agcaccttt cattctttca tatac        25

<210> SEQ ID NO 5
<211> LENGTH: 25
<212> TYPE: DNA
<213> ORGANISM: Artificial Sequence
<220> FEATURE:
<223> OTHER INFORMATION: Genomic DNA primer sequence

<400> SEQUENCE: 5
gacctcccca caggcatgat tgatc        25

<210> SEQ ID NO 6
<211> LENGTH: 25
<212> TYPE: DNA
<213> ORGANISM: Artificial Sequence
<220> FEATURE:
<223> OTHER INFORMATION: Primer in full length insert, 35S promoter to
      pat gene

<400> SEQUENCE: 6
tagaggacct aacagaactc gccgt        25

<210> SEQ ID NO 7
<211> LENGTH: 24
<212> TYPE: DNA
<213> ORGANISM: Artificial Sequence
<220> FEATURE:
<223> OTHER INFORMATION: Primer in full length insert, 35S promoter to
      pat gene

<400> SEQUENCE: 7
gagctggcaa ctcaaaatcc cttt        24

<210> SEQ ID NO 8
<211> LENGTH: 25
<212> TYPE: DNA
<213> ORGANISM: Artificial Sequence
<220> FEATURE:
<223> OTHER INFORMATION: Primer in full length insert, 35S promoter to
      pat gene

<400> SEQUENCE: 8
aaaatcttcg tcaacatggt ggagc        25

<210> SEQ ID NO 9
<211> LENGTH: 25
<212> TYPE: DNA
<213> ORGANISM: Artificial Sequence
<220> FEATURE:
<223> OTHER INFORMATION: Primer in full length insert, 35S promoter to
      pat gene

<400> SEQUENCE: 9
taatctcaac tggtctcctc tccgg        25

<210> SEQ ID NO 10

```
<211> LENGTH: 22
<212> TYPE: DNA
<213> ORGANISM: Artificial Sequence
<220> FEATURE:
<223> OTHER INFORMATION: Primer - Zea mays genomic DNA

<400> SEQUENCE: 10
cccctacccc accgacgttt at                                              22

<210> SEQ ID NO 11
<211> LENGTH: 22
<212> TYPE: DNA
<213> ORGANISM: Artificial Sequence
<220> FEATURE:
<223> OTHER INFORMATION: Primer - Zea mays genomic DNA

<400> SEQUENCE: 11
ttgattggca ggtccgtggg tc                                              22

<210> SEQ ID NO 12
<211> LENGTH: 22
<212> TYPE: DNA
<213> ORGANISM: Artificial Sequence
<220> FEATURE:
<223> OTHER INFORMATION: Primer - Zea mays genomic DNA

<400> SEQUENCE: 12
cacaacggca cagaaacacg aa                                              22

<210> SEQ ID NO 13
<211> LENGTH: 22
<212> TYPE: DNA
<213> ORGANISM: Artificial Sequence
<220> FEATURE:
<223> OTHER INFORMATION: Primer - Zea mays genomic DNA

<400> SEQUENCE: 13
gcgcacccac cggaacaaaa tg                                              22

<210> SEQ ID NO 14
<211> LENGTH: 22
<212> TYPE: DNA
<213> ORGANISM: Artificial Sequence
<220> FEATURE:
<223> OTHER INFORMATION: Primer - Zea mays genomic DNA

<400> SEQUENCE: 14
tcctcgcatt aaatgctcct gc                                              22

<210> SEQ ID NO 15
<211> LENGTH: 22
<212> TYPE: DNA
<213> ORGANISM: Artificial Sequence
<220> FEATURE:
<223> OTHER INFORMATION: Primer - Zea mays genomic DNA

<400> SEQUENCE: 15
cctggcacgc attgacgcat gt                                              22

<210> SEQ ID NO 16
<211> LENGTH: 25
<212> TYPE: DNA
<213> ORGANISM: Artificial Sequence
<220> FEATURE:
<223> OTHER INFORMATION: Primer - Zea mays genomic DNA

<400> SEQUENCE: 16
```

```
aagccgccac cgtcttgagg acctt                                           25
```

<210> SEQ ID NO 17
<211> LENGTH: 25
<212> TYPE: DNA
<213> ORGANISM: Artificial Sequence
<220> FEATURE:
<223> OTHER INFORMATION: Primer - Zea mays genomic DNA

<400> SEQUENCE: 17

```
gtcgaaccgt gcctccactt gctaa                                           25
```

<210> SEQ ID NO 18
<211> LENGTH: 25
<212> TYPE: DNA
<213> ORGANISM: Artificial Sequence
<220> FEATURE:
<223> OTHER INFORMATION: Primer - Zea mays genomic DNA

<400> SEQUENCE: 18

```
agaaagggaa aatcagggcc aggac                                           25
```

<210> SEQ ID NO 19
<211> LENGTH: 22
<212> TYPE: DNA
<213> ORGANISM: Artificial Sequence
<220> FEATURE:
<223> OTHER INFORMATION: Cry1F sequence primer

<400> SEQUENCE: 19

```
ggctcggact cgacctttct at                                              22
```

<210> SEQ ID NO 20
<211> LENGTH: 22
<212> TYPE: DNA
<213> ORGANISM: Artificial Sequence
<220> FEATURE:
<223> OTHER INFORMATION: Cry1F sequence primer

<400> SEQUENCE: 20

```
gcagttcttg aagaatgagt ga                                              22
```

<210> SEQ ID NO 21
<211> LENGTH: 2829
<212> TYPE: DNA
<213> ORGANISM: Artificial Sequence
<220> FEATURE:
<223> OTHER INFORMATION: 5' flanking sequence of event TC1507

<400> SEQUENCE: 21

```
actagttttcc tagcccgcgt cgtgccccta ccccaccgac gtttatggaa ggtgccattc     60
cacggttctt cgtggccgcc cctaaggatg taaatggtcg gtaaaatccg gtaaatttcc    120
ggtaccgttt accagatttt tccagccgtt ttcggattta tcgggatata cagaaaacga    180
gacggaaacg gaataggttt ttttcgaaa acggtacggt aaacggtgag acaaacttac    240
cgtccgtttt cgtatttctc gggaaactct ggtatattcc cgtatttgtc ccgtatttc     300
ccgacccacg gacctgccaa tcaaccatca gccagtcagc ccatcccccac agctatggcc    360
catgggccca tgttggccac atgcccacgc aacgcaaggc agtaaggctg cagcctggc     420
acgcattgac gcatgtggac acacacagcc gccgcctgtt cgtgtttctg tgccgttgtg    480
cgagactgtg actgcgagtg gcggagtcgg cgaacggcga ggcgtctccg gagtctggac    540
tgcggctgtg gacagcgacg ctgtgacggc gactcggcga agcccaaagc taccaagccc    600
```

```
ccaagtcccc atccatctct gcttctctgg tcatctcctt ccctggtcg atctgcaggc      660
gccagaccgg ccgaagcatc acgaaacgca ctaagacctc gaaggagtca aaccactcct     720
ccgaggcctc gggggctaca cccggcgggt gcgctcgcgc gcacccaccg gaacaaaatg     780
taaccgagaa aggtcggtcc ccttgcaaaa aaagtgcgac aaaagcctcc aagcgagtat     840
taacactcac tttgaggctc gggggctact gtcgggacc ataattaggg gtaccccaa       900
gactcctaat ctcagctggt aaccccatc agcacaaagc tgcaaaggcc tgatgggtgc      960
gattaagtca aggctcggtc cactcaaggg acacgatctc gcctcgcccg agcccagcct    1020
cgggcaaggg cggccgaccc cgaggattca cgtctcgccc gagggccccc tcaagcgacg    1080
ggcacacctt cggctcgccc gaggcccatt cttcgccgag aagcaaccct ggccagatcg    1140
ccacaccgac cgaccgtatc gcaggagcat ttaatgcgag gatcgcctga caccttatcc    1200
tgacgcgcgc tcttcagtcg acagagccga agtgaccgca atcacttcgc cgctccactg    1260
accgacctga caagaagaca gcgccgcctg cgtcgctccg actgctgtgc cactcgacag    1320
agtgaggctg acagcagcca agtccggcct cgggcgccat aggaagctcc gcctcgcccg    1380
accctagggc tcggactcgg cctcggctcc ggaagacgac gaactacgct tcgcccgacc    1440
ccagggcttg gactcagcct cggctccgga agacgacgaa ttccgcctcg ccgaccccca    1500
gggctcggac tcggcctcgg ctccagaaga cgacgaactc cgcctcgccc gaccccaggg    1560
ctcggactca gcctcggctc cggaagacga cgaactccgc ctcgcccgac ccagggctc     1620
ggactcagcc tcggcctcag acgatggtct ccgcctcgcc cgaccgggg ctcggactcg      1680
accttctctat cggaccttgt cagatcctgt cttcgtccga ggaggctttg gcaatcctca    1740
ctatgtactc ggtcttaggg gagtggcctt caacaaaact ggtacgaatc acacccgcac    1800
attcaggaac tccgggacca ttgactctct agatgagata ccacctcaag acaacagcgg    1860
cgcaccttgg aatgactact cccatgtgct gaatcatgtt accttttgtgc gctggccagg   1920
tgagatctca ggttccgact catggagagc accaatgttc tcttggacgc atcgtagcgc    1980
tacccccaca acaccattg atccagagag aatcactcat tcttcaagaa ctgcatatct     2040
tgccgagatc ctcatcccta aaggtacttg acaatagtat tattggagtc gatacacaac    2100
tcacaaaaaa tacaagaagt cgactaggtg gattggtccg agtgaagaga aaaaaaagcc    2160
atacagaact caaaatcttt tccggagata ttcatttcc tgaagaggcg gataagatat      2220
taggtggcag tttgatacca ccagaaagag aaaaaaaga ttctaaggaa tcaaaaaaaa      2280
ggaaaaattg ggtttatgtt caacggaaaa aatttctcaa aagcaaggaa aagtattgtg    2340
gctatttatc tatccgtgca gctgatatgg ccgcggtttg tgatatcgtt aaccattaca    2400
ttgagacgtc tacagtgaac tttaggacag agccacaaac accacaagag tggattgatg    2460
atctagagag gttgcaagat agataccctt ggttggttgc tgaggttgag ggtgttgtgg    2520
ctggtattgc ttacgctggg ccctggaagg ctaggaaccc tcaacctcag caaccaacca    2580
atggtatcta tcttgcaacc tctctagatc atcaatccac tcttgtggtg tttgtggctc    2640
tgtcctaaag ttcactgtag acgtctcaat gtaatggtta acgatatcac aaaccgagag    2700
aagagggatc tcgaagcttc ggccggggcc catcgatatc cgcgggcatg cctgcagtgc    2760
agcgtgaccc ggtcgtgccc ctctctagag ataatgagca ttgcatgtct aagttataaa    2820
aaattacca                                                             2829
```

<210> SEQ ID NO 22
<211> LENGTH: 2346
<212> TYPE: DNA

<213> ORGANISM: Artificial Sequence
<220> FEATURE:
<223> OTHER INFORMATION: 3' flanking sequence of event TC1507

<400> SEQUENCE: 22

| | | | | | |
|---|---|---|---|---|---|
| ctcactccgc | ttgatcttgg | caaagatatt | tgacgcattt | attagtatgt | gttaattttc | 60 |
| atttgcagtg | cagtattttc | tattcgatct | ttatgtaatt | cgttacaatt | aataaatatt | 120 |
| caaatcagat | tattgactgt | catttgtatc | aaatcgtgtt | taatggatat | ttttattata | 180 |
| atattgatga | tatctcaatc | aaaacgtaga | taataataat | atttatttaa | tattttgcg | 240 |
| tcgcacagtg | aaaatctata | tgagattaca | aaataccgac | aacattattt | aagaaacata | 300 |
| gacattaacc | ctgagactgt | tggacatcaa | cgggtagatt | ccttcatgca | tagcacctca | 360 |
| ttcttgggga | caaaagcacg | gtttggccgt | tccattgctg | cacgaacgag | ctttgctata | 420 |
| tcctcgggtt | ggatcatctc | atcaggtcca | atcaaatttg | tccaagaact | catgttagtc | 480 |
| gcaacgaaac | cggggcatat | gtcgggtatc | tcgagctcgc | gaaagcttgg | ctgcaggtcg | 540 |
| acggatcctt | caacaaaagg | gtacctgtac | ccgaaaccga | cacaggtggg | taggtagaga | 600 |
| atacctaggg | gcgcgagaca | actctctcta | aggaactcgg | caaaatagcc | ccgtaacttc | 660 |
| gggagaaggg | gtgcccccg | ctaacaataa | acgaatacgg | tttatgtatg | gattccggta | 720 |
| aaataccggt | actcgatttc | ataagagtcg | aataggaagt | taagatgagg | gtggtatcat | 780 |
| cataaaaatg | gagtagtatc | ctaaattata | ctaatccacg | tatgatatgt | atgcctttcc | 840 |
| ttatcaaccg | gaagtagtgc | aaaaaaaatt | ctatactgca | ctgctctctt | tttactgaga | 900 |
| aatgcaaaaa | aataaaagtg | aagtaagggt | gccccataga | tatttgatct | tgcctcctgt | 960 |
| ccccccccc | ctttttcat | caaaaatttc | catgaaaaaa | gaaagatgaa | atttgtccat | 1020 |
| tcattgaacc | ctagttcggg | actgacgggg | ctcgaacccg | cagcttccgc | ctgttcctag | 1080 |
| ccttccaggg | cccagcgtaa | gcaataccag | ccacagcacc | ctcaacctca | gcaaccaacc | 1140 |
| aagggtatct | atcttgcaac | ctctctagat | catcaatcca | ctcttgtggt | gtttgtggct | 1200 |
| ctgtcctaaa | gttcactgta | gacgtctcaa | tgtaatggtt | aacgatatca | caaaccgcgg | 1260 |
| aacacaagaa | cgaaagcacc | ttttcattct | ttcatatact | aggggttttt | acttggaaaa | 1320 |
| gacaatgttc | catactaaag | gatagctgca | gaagccgcca | ccgtcttgag | gaccttccgg | 1380 |
| ggagccagac | cggtcgaacc | gtgcctccac | ttgctaagga | gaagggaaa | atcagggcca | 1440 |
| ggacatacga | aggaggagcc | agaacgaaga | tatcctaaga | tacttactcg | ctccgggcca | 1500 |
| tgatcaatca | tgcctgtggg | gaggtctctc | gcacctcgat | ccatgaaggt | accaccgagg | 1560 |
| tctgccccgc | cgccggcttc | ggtaccgtcc | tcgccttggg | cgcccgaggc | acccggggga | 1620 |
| tggactgccc | aggcgcagcc | acgacgaccc | aaggatcacc | ctcctgcgca | gtcggcacga | 1680 |
| gcaatagttc | tcggggaaca | ggcagcttgg | cctgactccc | cggggtcacc | tcaactacct | 1740 |
| cggccgaggg | gtcaagtacc | ccctcagtcc | gccccgctc | tcggaccgg | accccgacg | 1800 |
| tcccggcccc | ggataccgac | ggcaccagcc | cgctcggggg | ctggcttgac | gaccctggc | 1860 |
| ccagcctcag | atctgggctg | aggccgaggc | aggcggccat | gtcgtcgtct | tcatcatcgt | 1920 |
| cttcatcatc | gtcgtcgtca | tcaggcgtct | ccggcgacgg | ctcccttggg | agcccctccc | 1980 |
| tctcctgccg | acgacgaagc | cttttccaagg | catcccgagc | ccacgtccgc | tcgtgggccc | 2040 |
| gagccttctt | tgcgtccttc | ttctccttcc | tcttctccgc | ggtgaccctc | cgcgcagctc | 2100 |
| ggtccaccgc | atcctccggg | actggtggca | ggaaggctt | tgatgccct | acctcctgga | 2160 |
| gacagacgaa | aagtctcagc | tatgagaacc | gagggcaatc | tgacgcaaga | aggaagaagg | 2220 |

```
                                                            -continued
agcggatact caccagagac acgcacccgc gatcgggacg cattaagggc tgggaaaaag    2280
tgccggcctc taatttcgct accgtgccgt ccacccacct gtggaggtca tcgatgggaa    2340
ggggaa                                                               2346

<210> SEQ ID NO 23
<211> LENGTH: 20
<212> TYPE: DNA
<213> ORGANISM: Artificial Sequence
<220> FEATURE:
<223> OTHER INFORMATION: Event specific primer sequence designed for
      TC1507

<400> SEQUENCE: 23
cttcaaacaa gtgtgacaaa                                                  20

<210> SEQ ID NO 24
<211> LENGTH: 11361
<212> TYPE: DNA
<213> ORGANISM: Artificial Sequence
<220> FEATURE:
<223> OTHER INFORMATION: The sequence represents the transgenic insert
      in maize line TC1507 as well as the sequence flanking the
      insertion sites.

<400> SEQUENCE: 24
actagtttcc tagcccgcgt cgtgccccta ccccaccgac gtttatggaa ggtgccattc      60
cacggttctt cgtggccgcc cctaaggatg taaatggtcg gtaaaatccg gtaaatttcc     120
ggtaccgttt accagatttt tccagccgtt ttcggattta tcgggatata cagaaaacga     180
gacggaaacg gaataggttt tttttcgaaa acggtacggt aaacggtgag acaaacttac     240
cgtccgtttt cgtatttctc gggaaactct ggtatattcc cgtatttgtc ccgtattttc     300
ccgacccacg gacctgccaa tcaaccatca gccagtcagc ccatcccac agctatggcc      360 catgggccca tgttggccac atgcccacgc aacgcaaggc agtaaggctg cagcctggc      420 acgcattgac gcatgtggac acacacagcc gccgcctgtt cgtgtttctg tgccgttgtg     480
cgagactgtg actgcgagtg gcggagtcgg cgaacggcga ggcgtctccg gagtctggac     540
tgcggctgtg gacagcgacg ctgtgacggc gactcggcga agccccaagc taccaagccc      600
ccaagtcccc atccatctct gcttctctgg tcatctcctt ccctggtcg atctgcaggc      660 gccagaccgg ccgaagcatc acgaaacgca ctaagacctc gaaggagtca aaccactcct     720
ccgaggcctc gggggctaca cccggcgggt gcgctcgcgc gcaccaccg gaacaaaatg       780 taaccgagaa aggtcggtcc ccttgcaaaa aaagtgcgac aaaagcctcc aagcgagtat     840
taacactcac tttgaggctc gggggctact gtcgggacc ataattaggg gtaccccaa       900 gactcctaat ctcagctggt aaccccatc agcacaaagc tgcaaaggcc tgatgggtgc      960
gattaagtca aggctcggtc cactcaaggg acacgatctc gcctcgcccg agcccagcct    1020
cgggcaaggg cggccgaccc cgaggattca cgtctcgccc gagggccccc tcaagcgacg    1080
ggcacacctt cggctcgccc gaggcccatt cttcgccgag aagcaaccgt ggccagatcg    1140
ccacaccgac cgaccgtatc gcaggagcat ttaatgcgag gatcgcctga caccttatcc    1200
tgacgcgcgc tcttcagtcg acagagccga agtgaccgca atcacttcgc cgctccactg    1260
accgacctga caagaagaca gcgccgcctg cgtcgctccg actgctgtgc cactcgacag    1320
agtgaggctg acagcagcca agtccggcct cgggcgccat aggaagctcc gcctcgcccg    1380
accctagggc tcggactcgg cctcggctcc ggaagacgac gaactacgct tcgcccgacc    1440
ccagggcttg gactcagcct cggctccgga agacgacgaa ttccgcctcg cccgacccca    1500
```

```
gggctcggac tcggcctcgg ctccagaaga cgacgaactc cgcctcgccc gaccccaggg    1560
ctcggactca gcctcggctc cggaagacga cgaactccgc ctcgcccgac cccagggctc    1620
ggactcagcc tcggcctcag acgatggtct ccgcctcgcc cgacccgggg ctcggactcg    1680 accttctat cggaccttgt cagatcctgt cttcgtccga ggaggctttg gcaatcctca     1740
ctatgtactc ggtcttaggg gagtggcctt caacaaact ggtacgaatc acacccgcac     1800
attcaggaac tccgggacca ttgactctct agatgagata ccacctcaag acaacagcgg    1860
cgcaccttgg aatgactact cccatgtgct gaatcatgtt acctttgtgc gctggccagg    1920
tgagatctca ggttccgact catggagagc accaatgttc tcttggacgc atcgtagcgc    1980
tacccccaca acaccattg atccagagag aatcactcat tcttcaagaa ctgcatatct     2040
tgccgagatc ctcatcccta aggtacttg acaatagtat tattggagtc gatacacaac     2100 tcacaaaaa tacaagaagt cgactaggtg gattggtccg agtgaagaga aaaaaaagcc     2160
atacagaact caaaatcttt tccggagata ttcattttcc tgaagaggcg ataagatat     2220 taggtggcag tttgatacca ccagaaagag aaaaaaaaga ttctaaggaa tcaaaaaaaa    2280
ggaaaaattg ggtttatgtt caacggaaaa aatttctcaa aagcaaggaa aagtattgtg    2340
gctatttatc tatccgtgca gctgatatgg ccgcggtttg tgatatcgtt aaccattaca    2400
ttgagacgtc tacagtgaac tttaggacag agccacaaac accacaagag tggattgatg    2460
atctagagag gttgcaagat agataccctt ggttggttgc tgaggttgag ggtgttgtgg    2520
ctggtattgc ttacgctggg ccctggaagg ctaggaaccc tcaacctcag caaccaacca    2580
atggtatcta tcttgcaacc tctctagatc atcaatccac tcttgtggtg tttgtggctc    2640
tgtcctaaag ttcactgtag acgtctcaat gtaatggtta acgatatcac aaaccgagag    2700
aagagggatc tcgaagcttc ggccggggcc catcgatatc cgcgggcatg cctgcagtgc    2760
agcgtgaccc ggtcgtgccc ctctctagag ataatgagca ttgcatgtct aagttataaa    2820
aaattaccac aactggaaga gcggttaccc ggaccgaagc ttcggccggg gcccatcgat    2880
atccgcgggc atgcctgcag tgcagcgtga cccggtcgtg cccctctcta gagataatga    2940
gcattgcatg tctaagttat aaaaaattac acatattttt ttttgtcaca cttgtttgaa    3000
gtgcagttta tctatctta tacatatatt taaactttac tctacgaata atataatcta     3060
tagtactaca ataatatcag tgttttagag aatcatataa atgaacagtt agacatggtc    3120
taaaggacaa ttgagtattt tgacaacagg actctacagt tttatctttt tagtgtgcat    3180
gtgttctcct ttttttttgc aaatagcttc acctatataa tacttcatcc attttattag    3240
tacatccatt tagggtttag ggttaatggt tttatagac taatttttt agtcacatcta     3300 tttattcta tttagcctc taaattaaga aaactaaaac tctattttag tttttttatt       3360
taataattta gatataaaat agaataaaat aaagtgacta aaaattaaac aaatacccct    3420
taagaaatta aaaaaactaa ggaaacattt ttcttgtttc gagtagataa tgccagcctg    3480
ttaaacgccg tcgacgagtc taacggacac caaccagcga accagcagcg tcgcgtcggg    3540
ccaagcgaag cagacggcac ggcatctctg tcgctgcctc tggacccctc tcgagagttc    3600
cgctccaccg ttggacttgc tccgctgtcg gcatccagaa attgcgtggc ggagcggcag    3660
acgtgagccg gcacggcagg cggcctcctc ctcctctcac ggcacggcag ctacggggga    3720 ttccttttccc accgctcctt cgctttccct tcctcgcccg ccgtaataaa tagacacccc    3780
ctccacaccc tctttcccca acctcgtgtt gttcggagcg cacacacaca caaccagatc    3840
tcccccaaat ccaccgtcg gcacctccgc ttcaaggtac gccgctcgtc ctcccccccc     3900
```

```
cccccctctct accttctcta gatcggcgtt ccggtccatg gttagggccc ggtagttcta    3960
cttctgttca tgtttgtgtt agatccgtgt ttgtgttaga tccgtgctgc tagcgttcgt    4020
acacggatgc gacctgtacg tcagacacgt tctgattgct aacttgccag tgtttctctt    4080
tggggaatcc tgggatggct ctagccgttc cgcagacggg atcgatttca tgattttttt    4140
tgtttcgttg catagggttt ggtttgccct tttcctttat ttcaatatat gccgtgcact    4200
tgtttgtcgg gtcatctttt catgctttt tttgtcttgg ttgtgatgat gtggtctggt    4260
tgggcggtcg ttctagatcg gagtagaatt ctgtttcaaa ctacctggtg gatttattaa    4320
ttttggatct gtatgtgtgt gccatacata ttcatagtta cgaattgaag atgatggatg    4380
gaaatatcga tctaggatag gtatacatgt tgatgcgggt tttactgatg catatacaga    4440
gatgcttttt gttcgcttgg ttgtgatgat gtggtgtggt tgggcggtcg ttcattcgtt    4500
ctagatcgga gtagaatact gtttcaaact acctggtgta tttattaatt ttggaactgt    4560
atgtgtgtgt catacatctt catagttacg agtttaagat ggatggaaat atcgatctag    4620
gataggtata catgttgatg tgggttttac tgatgcatat acatgatggc atatgcagca    4680
tctattcata tgctctaacc ttgagtacct atctattata taaacaagt atgttttata    4740 attattttga tcttgatata cttggatgat ggcatatgca gcagctatat gtggattttt    4800
ttagccctgc cttcatacgc tatttatttg cttggtactg tttcttttgt cgatgctcac    4860
cctgttgttt ggtgttactt ctgcaggtcg actctagagg atccaacaat ggagaacaac    4920
atacagaatc agtgcgtccc ctacaactgc ctcaacaatc ctgaagtaga gattctcaac    4980
gaagagaggt cgactggcag attgccgtta gacatctccc tgtcccttac acgtttcctg    5040
ttgtctgagt ttgttccagg tgtgggagtt gcgtttggcc tcttcgacct catctggggc    5100
ttcatcactc catctgattg gagcctctt cttctccaga ttgaacagtt gattgaacaa    5160
aggattgaga ccttggaaag gaatcgggcc atcactaccc ttcgtggctt agcagacagc    5220
tatgagatct acattgaagc actaagagag tgggaagcca atcctaacaa tgcccaactg    5280
agagaagatg tgcgtatacg ctttgctaac acagatgatg ctttgatcac agccatcaac    5340
aacttcaccc ttaccagctt cgagatccct cttctctcgg tctatgttca agctgctaac    5400
ctgcacttgt cactactgcg cgacgctgtg tcgtttgggc aaggttgggg actggacata    5460
gctactgtca acaatcacta caacagactc atcaatctga ttcatcgata cacgaaacat    5520
tgtttggata cctacaatca gggattggag aacctgagag gtactaacac tcgccaatgg    5580
gccaggttca atcagttcag gagagacctt acacttactg tgttagacat agttgctctc    5640
tttccgaact acgatgttcg tacctatccg attcaaacgt catcccaact tacaagggag    5700
atctacacca gttcagtcat tgaagactct ccagtttctg cgaacatacc caatggtttc    5760
aacagggctg agtttggagt cagaccaccc catctcatgg acttcatgaa ctctttgttt    5820
gtgactgcag agactgttag atcccaaact gtgtggggag acacttagt tagctcacgc    5880 aacacggctg gcaatcgtat caactttcct agttacgggg tcttcaatcc cggggggcgcc    5940 atctggattg cagatgaaga tccacgtcct ttctatcgga ccttgtcaga tcctgtcttc    6000
gtccgaggag gctttggcaa tcctcactat gtactcggtc ttaggggagt ggccttcaa    6060 caaactggta cgaatcacac ccgcacattc aggaactccg ggaccattga ctctctagat    6120
gagataccac tcaagacaa cagcggcgca ccttggaatg actactccca tgtgctgaat    6180
catgttacct ttgtgcgctg gccaggtgag atctcaggtt ccgactcatg gagagcacca    6240
atgttctctt ggacgcatcg tagcgctacc cccacaaaca ccattgatcc agagagaatc    6300
```

```
actcagattc ccttggtgaa ggcacacaca cttcagtcag gaactacagt tgtaagaggg    6360
ccggggttca cggaggagaa cattcttcga cgcactagtg gaggaccatt cgcgtacacc    6420
attgtcaaca tcaatgggca acttccccaa aggtatcgtg ccaggatacg ctatgcctct    6480
actaccaatc taagaatcta cgttacggtt gcaggtgaac ggatctttgc tggtcagttc    6540
aacaagacaa tggataccgg tgatccactt acattccaat ctttctccta cgccactatc    6600
aacaccgcgt tcacctttcc aatgagccag agcagtttca cagtaggtgc tgataccttc    6660
agttcaggca acgaagtgta cattgacagg tttgagttga ttccagttac tgccacactc    6720
gagtaaggat ccgtcgacct gcagccaagc tttcgcgagc tcgagatccc cgacatatgc    6780
cccggtttcg ttgcgactaa catgagttct tggacaaatt tgattggacc tgatgagatg    6840
atccaacccg aggatatagc aaagctcgtt cgtgcagcaa tggaacggcc aaaccgtgct    6900
tttgtcccca agaatgaggt gctatgcatg aaggaatcta cccgttgatg tccaacagtc    6960
tcagggttaa tgtctatgta tcttaaataa tgttgtcggt attttgtaat ctcatataga    7020
ttttcactgt gcgacgcaaa atattaaat aaatattatt attatctacg ttttgattga     7080
gatatcatca atattataat aaaaatatcc attaaacacg atttgataca aatgacagtc    7140
aataatctga tttgaatatt tattaattgt aacgaattac ataaagatcg aatagaaaat    7200
actgcactgc aaatgaaaat taacacatac taataaatgc gtcaaatatc tttgccaaga    7260
tcaagcggag tgagggcctc atatccggtc tcagttacaa gcacggtatc cccgaagcgc    7320
gctccaccaa tgccctcgac atagatgccg ggctcgacgc tgaggacatt gcctaccttg    7380
agcatggtct cagcgccggc tttaagctca atcccatccc aatctgaata tcctatcccg    7440
cgcccagtcc ggtgtaagaa cgggtctgtc catccacctc tgttgggaat tccggtccgg    7500
gtcacctttg tccaccaaga tggaactgcg gccgcggacc gaattcccat ggagtcaaag    7560
attcaaatag aggacctaac agaactcgcc gtaaagactg gcgaacagtt catacagagt    7620
ctcttacgac tcaatgacaa gaagaaaatc ttcgtcaaca tggtggagca cgacacgctt    7680
gtctactcca aaaatatcaa agatacagtc tcagaagacc aaagggcaat tgagactttt    7740
caacaaaggg taatatccgg aaacctcctc ggattccatt gcccagctat ctgtcacttt    7800
attgtgaaga tagtggaaaa ggaaggtggc tcctacaaat gccatcattg cgataaagga    7860
aaggccatcg ttgaagatgc ctctgccgac agtggtccca agatggaccc cccacccacg    7920
aggagcatcg tggaaaaaga agacgttcca accacgtctt caaagcaagt ggattgatgt    7980
gatatctcca ctgacgtaag ggatgacgca caatcccact atccttcgca agacccttcc    8040
tctatataag gaagttcatt tcatttggag aggacagggt acccggggat ccaccatgtc    8100
tccggagagg agaccagttg agattaggcc agctacagca gctgatatgg ccgcggtttg    8160
tgatatcgtt aaccattaca ttgagacgtc tacagtgaac tttaggacag agccacaaac    8220
accacaagag tggattgatg atctagagag gttgcaagat agatacccct ggttggttgc    8280
tgaggttgag ggtgttgtgg ctggtattgc ttacgctggg ccctggaagg ctaggaacgc    8340
ttacgattgg acagttgaga gtactgttta cgtgtcacat aggcatcaaa ggttgggcct    8400
aggatccaca ttgtacacac atttgcttaa gtctatggag gcgcaaggtt ttaagtctgt    8460
ggttgctgtt ataggccttc caaacgatcc atctgttagg ttgcatgagg ctttgggata    8520
cacagcccgg ggtacattgc gcgcagctgg atacaagcat ggtggatggc atgatgttgg    8580
tttttggcaa agggatttg agttgccagc tcctccaagg ccagttaggc cagttaccca     8640
gatctgagtc gacctgcagg catgcccgct gaaatcacca gtctctctct acaaatctat    8700
```

```
ctctctctat aataatgtgt gagtagttcc cagataaggg aattagggtt cttatagggt    8760
ttcgctcatg tgttgagcat ataagaaacc cttagtatgt atttgtattt gtaaaatact    8820
tctatcaata aaatttctaa ttcctaaaac caaaatccag tggcgagctc gaattcgagc    8880
tcgagcccgg gtggatcctc tagagtcgac ctgcagaagc ttcggtccgg cgcgcctcta    8940
gttgaagaca cgttcatgtc ttcatcgtaa aagacactc agtagtcttc ggccagaatg    9000
gcctaactca aggccctcac tccgcttgat cttggcaaag atatttgacg catttattag    9060
tatgtgttaa ttttcatttg cagtgcagta ttttctattc gatctttatg taattcgtta    9120
caattaataa atattcaaat cagattattg actgtcattt gtatcaaatc gtgtttaatg    9180 gatatttta ttataatatt gatgatatct caatcaaaac gtagataata ataatattta    9240
tttaatattt ttgcgtcgca cagtgaaaat ctatatgaga ttacaaaata ccgacaacat    9300
tatttaagaa acatagacat taaccctgag actgttggac atcaacgggt agattccttc    9360
atgcatagca cctcattctt ggggacaaaa gcacggtttg gccgttccat tgctgcacga    9420
acgagctttg ctatatcctc gggttggatc atctcatcag gtccaatcaa atttgtccaa    9480
gaactcatgt tagtcgcaac gaaaccgggg catatgtcgg gtatctcgag ctcgcgaaag    9540
cttggctgca ggtcgacgga tccttcaaca aagggtacc tgtacccgaa accgacacag    9600
gtgggtaggt agagaatacc tagggcgcg agacaactct ctctaaggaa ctcggcaaaa    9660
tagccccgta acttcgggag aaggggtgcc ccccgctaac aataaacgaa tacggtttat    9720
gtatggattc cggtaaaata ccggtactcg atttcataag agtcgaatag gaagttaaga    9780
tgagggtggt atcatcataa aaatggagta gtatcctaaa ttatactaat ccacgtatga    9840
tatgtatgcc tttccttatc aaccggaagt agtgcaaaaa aaattctata ctgcactgct    9900 ctcttttac tgagaaatgc aaaaaaataa aagtgaagta agggtgcccc atagatattt    9960
gatcttgcct cctgtccccc ccccctttt ttcatcaaaa atttccatga aaaaagaaaa    10020
gatgaatttg tccattcatt gaaccctagt tcgggactga cggggctcga acccgcagct    10080
tccgcctgtt cctagccttc cagggcccag cgtaagcaat accagccaca gcaccctcaa    10140
cctcagcaac caaccaaggg tatctatctt gcaacctctc tagatcatca atccactctt    10200
gtggtgtttg tggctctgtc ctaaagttca ctgtagacgt tcaatgtaa tggttaacga    10260 tatcacaaac cgcggaacac aagaacgaaa gcaccttttc attctttcat atactagggg    10320
tttttacttg gaaaagacaa tgttccatac taaaggatag ctgcagaagc cgccaccgtc    10380
ttgaggacct tccggggagc cagaccggtc gaaccgtgcc tccacttgct aaggagaaag    10440
ggaaaatcag ggccaggaca tacgaaggag agccagaac gaagatatcc taagatactt    10500
actcgctccg ggccatgatc aatcatgcct gtggggaggt ctctcgcacc tcgatccatg    10560
aaggtaccac cgaggtctgc cccgccgccg gcttcggtac cgtcctcgcc ttgggcgccc    10620
gaggcacccg ggggatggac tgcccaggcg cagccacgac gacccaagga tcaccctcct    10680
gcgcagtcgg cacgagcaat agttctcggg gaacaggcag cttggcctga ctccccgggg    10740
tcacctcaac tacctcggcc gagggtcaa gtaccccctc agtccgcccc cgtcttcgg    10800 accgggaccc cgacgtcccg gcccggata ccgacggcac cagcccgctc ggggctggc    10860 ttgacgaccc ctgcccagc ctcagatctg ggctgaggcc gaggcaggcg gccatgtcgt    10920
cgtcttcatc atcgtcttca tcatcgtcgt cgtcatcagg cgtctccggc gacggctccc    10980
ttgggagccc ctccctctcc tgccgacgac gaagcctttc caaggcatcc cgagcccacg    11040
tccgctcgtg ggcccgagcc ttcttttgcgt ccttcttctc cttcctcttc tccgcggtga    11100
```

-continued

| | |
|---|---|
| ccctccgcgc agctcggtcc accgcatcct ccgggactgg tggcagggaa ggcttgtgat | 11160 |
| gccctacctc ctggagacag acgaaaagtc tcagctatga gaaccgaggg caatctgacg | 11220 |
| caagaaggaa gaaggagcgg atactccacca gagacacgca cccgcgatcg ggacgcatta | 11280 |
| agggctggga aaaagtgccg gcctctaatt tcgctaccgt gccgtccacc cacctgtgga | 11340 |
| ggtcatcgat gggaagggga a | 11361 |

<210> SEQ ID NO 25
<211> LENGTH: 6186
<212> TYPE: DNA
<213> ORGANISM: Artificial Sequence
<220> FEATURE:
<223> OTHER INFORMATION: The sequence represents the DNA molecule used
    to transform maize line TC1507. This sequence represents insert
    PHI8999A.

<400> SEQUENCE: 25

| | |
|---|---|
| caactggaag agcggttacc cggaccgaag cttcggccgg ggcccatcga tatccgcggg | 60 |
| catgcctgca gtgcagcgtg acccggtcgt gcccctctct agagataatg agcattgcat | 120 |
| gtctaagtta taaaaaatta ccacatattt tttttgtcac acttgtttga agtgcagttt | 180 |
| atctatcttt atacatatat ttaaacttta ctctacgaat aatataatct atagtactac | 240 |
| aataatatca gtgttttaga gaatcatata aatgaacagt tagacatggt ctaaaggaca | 300 |
| attgagtatt ttgacaacag gactctacag ttttatcttt ttagtgtgca tgtgttctcc | 360 |
| ttttttttg caaatagctt cacctatata atacttcatc catttttatta gtacatccat | 420 |
| ttagggttta gggttaatgg ttttttataga ctaattttttt tagtacatct atttttattct | 480 |
| attttagcct ctaaattaag aaaactaaaa ctctatttta gttttttttat ttaataatttt | 540 |
| agatataaaa tagaataaaa taaagtgact aaaaattaaa caaatacccct taagaaatt | 600 |
| aaaaaaacta aggaaacatt tttcttgttt cgagtagata atgccagcct gttaaacgcc | 660 |
| gtcgacgagt ctaacggaca ccaaccagcg aaccagcagc gtcgcgtcgg gccaagcgaa | 720 |
| gcagacggca cggcatctct gtcgctgcct ctggaccccct ctcgagagtt ccgctccacc | 780 |
| gttggacttg ctccgctgtc ggcatccaga aattgcgtgg cggagcggca gacgtgagcc | 840 |
| ggcacggcag gcggcctcct cctcctctca cggcacggca gctacggggg attcctttcc | 900 |
| caccgctcct tcgctttccc ttcctcgccc gccgtaataa atagacaccc cctccacacc | 960 |
| ctctttcccc aacctcgtgt tgttcggagc gcacacacac acaaccagat ctcccccaaa | 1020 |
| tccacccgtc ggcacctccg cttcaaggta cgccgctcgt cctccccccc ccccctctc | 1080 |
| taccttctct agatcggcgt tccggtccat ggttagggcc cggtagttct acttctgttc | 1140 |
| atgtttgtgt tagatccgtg tttgtgttag atccgtgctg ctagcgttcg tacacggatg | 1200 |
| cgacctgtac gtcagacacg ttctgattgc taacttgcca gtgtttctct ttggggaatc | 1260 |
| ctgggatggc tctagccgtt ccgcagacgg gatcgatttc atgatttttt ttgtttcgtt | 1320 |
| gcatagggtt tggtttgccc ttttcctta tttcaatata tgccgtgcac ttgtttgtcg | 1380 |
| ggtcatcttt tcatgctttt ttttgtcttg gttgtgatga tgtggtctgg ttgggcggtc | 1440 |
| gttctagatc ggagtagaat tctgtttcaa actacctggt ggatttatta attttggatc | 1500 |
| tgtatgtgtg tgccatacat attcatagtt acgaattgaa gatgatggat ggaaatatcg | 1560 |
| atctaggata ggtatacatg ttgatgcggg ttttactgat gcatatacag agatgctttt | 1620 |
| tgttcgcttg gttgtgatga tgtggtgtgg ttgggcggtc gttcattcgt tctagatcgg | 1680 |
| agtagaatac tgtttcaaac tacctggtgt atttattaat tttggaactg tatgtgtgtg | 1740 |

```
tcatacatct tcatagttac gagtttaaga tggatggaaa tatcgatcta ggataggtat    1800
acatgttgat gtgggtttta ctgatgcata tacatgatgg catatgcagc atctattcat    1860
atgctctaac cttgagtacc tatctattat aataaacaag tatgttttat aattattttg    1920
atcttgatat acttggatga tggcatatgc agcagctata tgtggatttt tttagccctg    1980
ccttcatacg ctatttattt gcttggtact gtttcttttg tcgatgctca ccctgttgtt    2040
tggtgttact tctgcaggtc gactctagag gatccaacaa tggagaacaa catacagaat    2100
cagtgcgtcc cctacaactg cctcaacaat cctgaagtag agattctcaa cgaagagagg    2160
tcgactggca gattgccgtt agacatctcc ctgtccctta cacgtttcct gttgtctgag    2220
tttgttccag gtgtgggagt tgcgtttggc ctcttcgacc tcatctgggg cttcatcact    2280
ccatctgatt ggagcctctt tcttctccag attgaacagt tgattgaaca aaggattgag    2340
accttggaaa ggaatcgggc catcactacc cttcgtggct agcagacag ctatgagatc    2400
tacattgaag cactaagaga gtgggaagcc aatcctaaca atgcccaact gagagaagat    2460
gtgcgtatac gctttgctaa cacagatgat gctttgatca cagccatcaa caacttcacc    2520
cttaccagct tcgagatccc tcttctctcg gtctatgttc aagctgctaa cctgcacttg    2580
tcactactgc gcgacgctgt gtcgtttggg caaggttggg gactggacat agctactgtc    2640
aacaatcact acaacagact catcaatctg attcatcgat acacgaaaca ttgtttggat    2700
acctacaatc agggattgga gaacctgaga ggtactaaca ctcgccaatg ggccaggttc    2760
aatcagttca ggagagacct tacacttact gtgttagaca tagttgctct cttttccgaac    2820
tacgatgttc gtacctatcc gattcaaacg tcatcccaac ttacaaggga gatctacacc    2880
agttcagtca ttgaagactc tccagtttct gcgaacatac ccaatggttt caacagggct    2940
gagtttggag tcagaccacc ccatctcatg gacttcatga actctttgtt tgtgactgca    3000
gagactgtta gatcccaaac tgtgtgggga ggacacttag ttagctcacg caacacggct    3060
ggcaatcgta tcaactttcc tagttacggg gtcttcaatc ccggggcgc catctggatt    3120
gcagatgaag atccacgtcc tttctatcgg accttgtcag atcctgtctt cgtccgagga    3180
ggctttggca atcctcacta tgtactcggt cttaggggag tggccttttca acaaactggt    3240
acgaatcaca cccgcacatt caggaactcc gggaccattg actctctaga tgagatacca    3300
cctcaagaca acagcggcgc accttggaat gactactccc atgtgctgaa tcatgttacc    3360
tttgtgcgct ggccaggtga gatctcaggt tccgactcat ggagagcacc aatgttctct    3420
tggacgcatc gtagcgctac ccccacaaac accattgatc cagagagaat cactcagatt    3480
cccttggtga aggcacacac acttcagtca ggaactacag ttgtaagagg gccgggttc    3540
acgggaggag acattcttcg acgcactagt ggaggaccat tcgcgtacac cattgtcaac    3600
atcaatgggc aacttcccca aaggtatcgt gccaggatac gctatgcctc tactaccaat    3660
ctaagaatct acgttacggt tgcaggtgaa cggatctttg ctggtcagtt caacaagaca    3720
atggataccg gtgatccact tacattccaa tctttctcct acgccactat caacaccgcg    3780
ttcacctttc caatgagcca gagcagtttc acagtaggtg ctgatacctt cagttcaggc    3840
aacgaagtgt acattgacag gtttgagttg attccagtta ctgccacact cgagtaagga    3900
tccgtcgacc tgcagccaag cttttcgcga gctcgagatc cccgacatat gccccggttt    3960
cgttgcgact aacatgagtt cttggacaaa tttgattgga cctgatgaga tgatccaacc    4020
cgaggatata gcaaagctcg ttcgtgcagc aatggaacgg ccaaaccgtg cttttgtccc    4080
caagaatgag gtgctatgca tgaaggaatc tacccgttga tgtccaacag tctcagggtt    4140
```

```
aatgtctatg tatcttaaat aatgttgtcg gtattttgta atctcatata gattttcact    4200
gtgcgacgca aaaatattaa ataaatatta ttattatcta cgttttgatt gagatatcat    4260
caatattata ataaaaatat ccattaaaca cgatttgata caaatgacag tcaataatct    4320
gatttgaata tttattaatt gtaacgaatt acataaagat cgaatagaaa atactgcact    4380
gcaaatgaaa attaacacat actaataaat gcgtcaaata tctttgccaa gatcaagcgg    4440
agtgagggcc tcatatccgg tctcagttac aagcacggta tccccgaagc gcgctccacc    4500
aatgccctcg acatagatgc cgggctcgac gctgaggaca ttgcctacct tgagcatggt    4560
ctcagcgccg gctttaagct caatcccatc ccaatctgaa tatcctatcc cgcgcccagt    4620
ccggtgtaag aacgggtctg tccatccacc tctgttggga attccggtcc gggtcacctt    4680
tgtccaccaa gatggaactg cggccgcgga ccgaattccc atggagtcaa agattcaaat    4740
agaggaccta acagaactcg ccgtaaagac tggcgaacag ttcatacaga gtctcttacg    4800
actcaatgac aagaagaaaa tcttcgtcaa catggtggag cacgcacacg ttgtctactc    4860
caaaaatatc aaagatacag tctcagaaga ccaaagggca attgagactt tcaacaaag    4920
ggtaatatcc ggaaacctcc tcggattcca ttgcccagct atctgtcact ttattgtgaa    4980
gatagtggaa aaggaaggtg gctcctacaa atgccatcat tgcgataaag gaaaggccat    5040
cgttgaagat gcctctgccg acagtggtcc caaagatgga cccccaccca cgaggagcat    5100
cgtggaaaaa gaagacgttc caaccacgtc ttcaaagcaa gtggattgat gtgatatctc    5160
cactgacgta agggatgacg cacaatccca ctatccttcg caagacccct cctctatata    5220
aggaagttca tttcatttgg agaggacagg gtacccgggg atccaccatg tctccggaga    5280
ggagaccagt tgagattagg ccagctacag cagctgatat ggccgcggtt tgtgatatcg    5340
ttaaccatta cattgagacg tctacagtga actttaggac agagccacaa acaccacaag    5400
agtggattga tgatctagag aggttgcaag atagataccc ttggttggtt gctgaggttg    5460
agggtgttgt ggctggtatt gcttacgctg ggccctggaa ggctaggaac gcttacgatt    5520
ggacagttga gagtactgtt tacgtgtcac ataggcatca aaggttgggc ctaggatcca    5580
cattgtacac acatttgctt aagtctatgg aggcgcaagg ttttaagtct gtggttgctg    5640
ttataggcct tccaaacgat ccatctgtta ggttgcatga ggctttggga tacacagccc    5700
ggggtacatt gcgcgcagct ggatacaagc atggtggatg gcatgatgtt ggttttttggc    5760
aaagggattt tgagttgcca gctcctccaa ggccagttag gccagttacc cagatctgag    5820
tcgacctgca ggcatgccgc tgaaatcacc agtctctctc tacaaatcta tctctctcta    5880
taataatgtg tgagtagttc ccagataagg gaattagggt tcttataggg tttcgctcat    5940
gtgttgagca tataagaaac ccttagtatg tatttgtatt tgtaaaatac ttctatcaat    6000
aaaatttcta attcctaaaa ccaaaatcca gtggcgagct cgaattcgag ctcgagcccg    6060
ggtggatcct ctagagtcga cctgcagaag cttcggtccg gcgcgcctct agttgaagac    6120
acgttcatgt cttcatcgta agaagacact cagtagtctt cggccagaat ggcctaactc    6180
aaggcc                                                              6186
```

<210> SEQ ID NO 26
<211> LENGTH: 3830
<212> TYPE: DNA
<213> ORGANISM: Artificial Sequence
<220> FEATURE:
<223> OTHER INFORMATION: Sequence that represents part of the PHI8999A
      insert as well as flanking sequence 5' to the insert.

<400> SEQUENCE: 26

```
actagtttcc tagcccgcgt cgtgccccta ccccaccgac gtttatggaa ggtgccattc      60
cacggttctt cgtggccgcc cctaaggatg taaatggtcg gtaaaatccg gtaaatttcc     120
ggtaccgttt accagatttt tccagccgtt ttcggattta tcgggatata cagaaaacga     180
gacggaaacg gaataggttt tttttcgaaa acggtacggt aaacggtgag acaaacttac     240
cgtccgtttt cgtatttctc gggaaactct ggtatattcc cgtatttgtc ccgtatttc      300
ccgacccacg gacctgccaa tcaaccatca gccagtcagc ccatcccac agctatggcc      360
catggggcca tgttggccac atgcccacgc aacgcaaggc agtaaggctg gcagcctggc     420
acgcattgac gcatgtggac acacacagcc gccgcctgtt cgtgtttctg tgccgttgtg     480
cgagactgtg actgcgagtg gcggagtcgg cgaacggcga ggcgtctccg gagtctggac     540
tgcggctgtg gacagcgacg ctgtgacggc gactcggcga agccccaagc taccaagccc     600
ccaagtcccc atccatctct gcttctctgg tcatctcctt ccctggtcg atctgcaggc      660
gccagaccgg ccgaagcatc acgaaacgca ctaagacctc gaaggagtca aaccactcct     720
ccgaggcctc gggggctaca cccggcgggt gcgctcgcgc gcacccaccg gaacaaaatg     780
taaccgagaa aggtcggtcc ccttgcaaaa aaagtgcgac aaaagcctcc aagcgagtat     840
taacactcac tttgaggctc gggggctact gtcggggacc ataattaggg gtaccccaa      900
gactcctaat ctcagctggt aaccccatc agcacaaagc tgcaaaggcc tgatgggtgc      960
gattaagtca aggctcggtc cactcaaggg acacgatctc gcctcgcccg agcccagcct    1020
cgggcaaggg cggccgaccc cgaggattca cgtctcgccc gagggccccc tcaagcgacg    1080
ggcacacctt cggctcgccc gaggcccatt cttcgccgag aagcaaccett ggccagatcg    1140
ccacaccgac cgaccgtatc gcaggagcat ttaatgcgag gatcgcctga caccttatcc    1200
tgacgcgcgc tcttcagtcg acagagccga agtgaccgca atcacttcgc cgctccactg    1260
accgacctga caagaagaca gcgccgcctg cgtcgctccg actgctgtgc cactcgacag    1320
agtgaggctg acagcagcca agtccggcct cgggcgccat aggaagctcc gcctcgcccg    1380
acctagggc tcggactcgg cctcggctcc ggaagacgac gaactacgct tcgcccgacc    1440
ccagggcttg gactcagcct cggctccgga agacgacgaa ttccgcctcg cccgacccca    1500
gggctcggac tcggcctcgg ctccagaaga cgacgaactc cgcctcgccc gaccccaggg    1560
ctcggactca gcctcggctc cggaagacga cgaactccgc ctcgcccgac cccagggctc    1620
ggactcagcc tcggcctcag acgatggtct ccgcctcgcc cgaccggggg ctcggactcg    1680
acctttctat cggaccttgt cagatcctgt cttcgtccga ggaggctttg gcaatcctca    1740
ctatgtactc ggtcttaggg gagtggcctt tcaacaaact ggtacgaatc acacccgcac    1800
attcaggaac tccgggacca ttgactctct agatgagata ccacctcaag caacagcgg     1860
cgcaccttgg aatgactact cccatgtgct gaatcatgtt acctttgtgc gctggccagg    1920
tgagatctca ggttccgact catggagagc accaatgttc tcttggacgc atcgtagcgc    1980
tacccccaca acaccattg atccagagag aatcactcat tcttcaagaa ctgcatatct    2040
tgccgagatc ctcatcccta aggtacttg acaatagtat tattggagtc gatacacaac     2100
tcacaaaaaa tacaagaagt cgactaggtg gattggtccg agtgaagaga aaaaaaagcc    2160
atacagaact caaaatcttt tccggagata ttcattttcc tgaagaggcg gataagatat    2220
taggtggcag tttgatacca ccagaaaaag aaaaaaaaga ttctaaggaa tcaaaaaaaa    2280
ggaaaaattg ggtttatgtt caacggaaaa aatttctcaa aagcaaggaa aagtattgtg    2340
```

```
gctatttatc tatccgtgca gctgatatgg ccgcggtttg tgatatcgtt aaccattaca    2400
ttgagacgtc tacagtgaac tttaggacag agccacaaac accacaagag tggattgatg    2460
atctagagag gttgcaagat agataccctt ggttggttgc tgaggttgag ggtgttgtgg    2520
ctggtattgc ttacgctggg ccctggaagg ctaggaaccc tcaacctcag caaccaacca    2580
atggtatcta tcttgcaacc tctctagatc atcaatccac tcttgtggtg tttgtggctc    2640
tgtcctaaag ttcactgtag acgtctcaat gtaatggtta acgatatcac aaaccgagag    2700
aagagggatc tcgaagcttc ggccggggcc catcgatatc cgcgggcatg cctgcagtgc    2760
agcgtgaccc ggtcgtgccc ctctctagag ataatgagca ttgcatgtct aagttataaa    2820
aaattaccac aactggaaga gcggttaccc ggaccgaagc ttcggccggg gcccatcgat    2880
atccgcgggc atgcctgcag tgcagcgtga cccggtcgtg cccctctcta gagataatga    2940
gcattgcatg tctaagttat aaaaaattac acatattttt ttttgtcaca cttgtttgaa    3000
gtgcagttta tctatcttta tacatatatt taaactttac tctacgaata atataatcta    3060
tagtactaca ataatatcag tgttttagag aatcatataa atgaacagtt agacatggtc    3120
taaaggacaa ttgagtattt tgacaacagg actctacagt tttatctttt tagtgtgcat    3180
gtgttctcct ttttttttgc aaatagcttc acctatataa tacttcatcc attttattag    3240
tacatccatt tagggtttag ggttaatggt ttttatagac taattttttt agtacatcta    3300
ttttattcta ttttagcctc taaattaaga aaactaaaac tctattttag ttttttatt     3360 taataattta gatataaaat agaataaaat aaagtgacta aaaattaaac aaatacccct    3420
taagaaatta aaaaaactaa ggaaacattt ttcttgtttc gagtagataa tgccagcctg    3480
ttaaacgccg tcgacgagtc taacggacac caaccagcga accagcagcg tcgcgtcggg    3540
ccaagcgaag cagacggcac ggcatctctg tcgctgcctc tggaccctc tcgagagttc     3600 cgctccaccg ttggacttgc tccgctgtcg gcatccagaa attgcgtggc ggagcggcag    3660
acgtgagccg gcacggcagg cggcctcctc ctcctctcac ggcacggcag ctacggggga    3720
ttcctttccc accgctcctt cgctttccct tcctcgcccg ccgtaataaa tagacacccc    3780
ctccacaccc tctttccccca acctcgtgtt gttcggagcg cacacacaca               3830
```

<210> SEQ ID NO 27
<211> LENGTH: 3347
<212> TYPE: DNA
<213> ORGANISM: Artificial Sequence
<220> FEATURE:
<223> OTHER INFORMATION: Sequence that represents part of the PHI8999A
      insert as well as flanking sequence 3' to the
      insert.

<400> SEQUENCE: 27

```
cccactatcc ttcgcaagac ccttcctcta tataaggaag ttcatttcat ttggagagga     60
cagggtaccc ggggatccac catgtctccg gagaggagac cagttgagat taggccagct    120
acagcagctg atatggccgc ggtttgtgat atcgttaacc attacattga cgtctacaa    180 gtgaacttta ggacagagcc acaaacacca caagagtgga ttgatgatct agagaggttg    240
caagatagat acccttggtt ggttgctgag gttgagggtg ttgtggctgg tattgcttac    300
gctgggccct ggaaggctag gaacgcttac gattggacag ttgagagtac tgtttacgtg    360
tcacataggc atcaaaggtt gggcctagga tccacattgt acacacattt gcttaagtct    420
atggaggcgc aaggttttaa gtctgtggtt gctgttatag ccttccaaa cgatccatct     480 gttaggttgc atgaggcttt gggatacaca gcccggggta cattgcgcgc agctggatac    540
```

-continued

| | | |
|---|---|---|
| aagcatggtg gatggcatga tgttggtttt tggcaaaggg attttgagtt gccagctcct | 600 |
| ccaaggccag ttaggccagt tacccagatc tgagtcgacc tgcaggcatg cccgctgaaa | 660 |
| tcaccagtct ctctctacaa atctatctct ctctataata atgtgtgagt agttcccaga | 720 |
| taagggaatt agggttctta tagggtttcg ctcatgtgtt gagcatataa gaaacccttta | 780 |
| gtatgtattt gtatttgtaa aatacttcta tcaataaaat ttctaattcc taaaaccaaa | 840 |
| atccagtggc gagctcgaat tcgagctcga gcccggtgg atcctctaga gtcgacctgc | 900 |
| agaagcttcg gtccggcgcg cctctagttg aagcacgtt catgtcttca tcgtaagaag | 960 |
| acactcagta gtcttcggcc agaatggcct aactcaaggc cctcactccg cttgatcttg | 1020 |
| gcaaagatat ttgacgcatt tattagtatg tgttaatttt catttgcagt gcagtatttt | 1080 |
| ctattcgatc tttatgtaat tcgttacaat taataaatat tcaaatcaga ttattgactg | 1140 |
| tcatttgtat caaatcgtgt ttaatggata ttttattat aatattgatg atatctcaat | 1200 |
| caaaacgtag ataataataa tatttattta atattttgc gtcgcacagt gaaaatctat | 1260 |
| atgagattac aaaataccga caacattatt taagaaacat agacattaac cctgagactg | 1320 |
| ttggacatca acgggtagat tccttcatgc atagcacctc attcttgggg acaaaagcac | 1380 |
| ggtttggccg ttccattgct gcacgaacga gctttgctat atcctcgggt tggatcatct | 1440 |
| catcaggtcc aatcaaattt gtccaagaac tcatgttagt cgcaacgaaa ccggggcata | 1500 |
| tgtcgggtat ctcgagctcg cgaaagcttg gctgcaggtc gacggatcct tcaacaaaag | 1560 |
| ggtacctgta cccgaaaccg acacaggtgg gtaggtagag aatacctagg ggcgcgagac | 1620 |
| aactctctct aaggaactcg gcaaaatagc cccgtaactt cgggagaagg ggtgccccccc | 1680 |
| gctaacaata aacgaatacg gtttatgtat ggattccggt aaaataccgg tactcgattt | 1740 |
| cataagagtc gaataggaag ttaagatgag ggtggtatca tcataaaaat ggagtagtat | 1800 |
| cctaaattat actaatccac gtatgatatg tatgcctttc cttatcaacc ggaagtagtg | 1860 |
| caaaaaaaat tctatactgc actgctctct ttttactgag aaatgcaaaa aaataaaagt | 1920 |
| gaagtaaggg tgccccatag atatttgatc ttgcctcctg tcccccccc ccttttttca | 1980 |
| tcaaaaattt ccatgaaaaa agaaaagatg aatttgtcca ttcattgaac cctagttcgg | 2040 |
| gactgacggg gctcgaaccc gcagcttccg cctgttccta gccttccagg gcccagcgta | 2100 |
| agcaatacca gccacagcac cctcaacctc agcaaccaac caagggtatc tatcttgcaa | 2160 |
| cctctctaga tcatcaatcc actcttgtgg tgtttgtggc tctgtcctaa agttcactgt | 2220 |
| agacgtctca atgtaatggt taacgatatc acaaaccgcg gaacacaaga acgaaagcac | 2280 |
| cttttcattc tttcatatac tagggggtttt tacttggaaa agacaatgtt ccatactaaa | 2340 |
| ggatagctgc agaagccgcc accgtcttga ggaccttccg gggagccaga ccggtcgaac | 2400 |
| cgtgcctcca cttgctaagg agaaagggaa aatcagggcc aggacatacg aaggaggagc | 2460 |
| cagaacgaag atatcctaag atacttactc gctccgggcc atgatcaatc atgcctgtgg | 2520 |
| ggaggtctct cgcacctcga tccatgaagg taccaccgag gtctgccccg ccgccggctt | 2580 |
| cggtaccgtc ctcgccttgg gcgcccgagg caccccgggg atggactgcc caggcgcagc | 2640 |
| cacgacgacc caaggatcac cctcctgcgc agtcggcacg agcaatagtt ctcggggaac | 2700 |
| aggcagcttg gcctgactcc ccggggtcac ctcaactacc tcggccgagg ggtcaagtac | 2760 |
| cccctcagtc cgcccccgct cttcggaccg ggaccccgac gtcccggccc cggataccga | 2820 |
| cggcaccagc ccgctcgggg gctggcttga cgacccctgg cccagcctca gatctgggct | 2880 |
| gaggccgagg caggcggcca tgtcgtcgtc ttcatcatcg tcttcatcat cgtcgtcgtc | 2940 |

```
atcaggcgtc tccggcgacg gctcccttgg gagcccctcc ctctcctgcc gacgacgaag    3000
cctttccaag gcatcccgag cccacgtccg ctcgtgggcc cgagccttct ttgcgtcctt    3060
cttctccttc ctcttctccg cggtgaccct ccgcgcagct cggtccaccg catcctccgg    3120
gactggtggc agggaaggct tgtgatgccc tacctcctgg agacagacga aaagtctcag    3180
ctatgagaac cgagggcaat ctgacgcaag aaggaagaag gagcggatac tcaccagaga    3240
cacgcacccg cgatcgggac gcattaaggg ctgggaaaaa gtgccggcct ctaatttcgc    3300
taccgtgccg tccacccacc tgtggaggtc atcgatggga agggaa                   3347
```

<210> SEQ ID NO 28
<211> LENGTH: 669
<212> TYPE: DNA
<213> ORGANISM: Zea mays

<400> SEQUENCE: 28

```
actagtttcc tagcccgcgt cgtgccccta ccccaccgac gtttatggaa ggtgccattc     60
cacggttctt cgtggccgcc cctaaggatg taaatggtcg gtaaaatccg gtaaatttcc    120
ggtaccgttt accagatttt tccagccgtt ttcggattta tcgggatata cagaaaacga    180
gacggaaacg gaataggttt tttttcgaaa acggtacggt aaacggtgag acaaacttac    240
cgtccgtttt cgtatttctc gggaaactct ggtatattcc cgtatttgtc ccgtattttc    300
ccgacccacg gacctgccaa tcaaccatca gccagtcagc ccatccccac agctatggcc    360
catgggccca tgttggccac atgcccacgc aacgcaaggc agtaaggctg gcagcctggc    420
acgcattgac gcatgtggac acacacagcc gccgcctgtt cgtgtttctg tgccgttgtg    480
cgagactgtg actgcgagtg gcggagtcgg cgaacggcga ggcgtctccg gagtctggac    540
tgcggctgtg gacagcgacg ctgtgacggc gactcggcga agccccaagc taccaagccc    600
ccaagtcccc atccatctct gcttctctgg tcatctcctt ccctggtcg atctgcaggc    660 gccagaccg                                                            669
```

<210> SEQ ID NO 29
<211> LENGTH: 200
<212> TYPE: DNA
<213> ORGANISM: Zea mays

<400> SEQUENCE: 29

```
gccgaagcat cacgaaacgc actaagacct cgaaggagtc aaaccactcc tccgaggcct     60
cgggggctac acccggcggg tgcgctcgcg cgcacccacc ggaacaaaat gtaaccgaga    120
aaggtcggtc cccttgcaaa aaaagtgcga caaaagcctc caagcgagta ttaacactca    180
ctttgaggct cggggggctac                                                200
```

<210> SEQ ID NO 30
<211> LENGTH: 812
<212> TYPE: DNA
<213> ORGANISM: Zea mays
<220> FEATURE:
<221> NAME/KEY: misc_feature
<222> LOCATION: (0)...(0)
<223> OTHER INFORMATION: Fragment of maize Huck-1 retrotransposon

<400> SEQUENCE: 30

```
tgtcggggac cataattagg ggtaccccca agactcctaa tctcagctgg taaccccat      60 cagcacaaag ctgcaaaggc ctgatgggtg cgattaagtc aaggctcggt ccactcaagg    120
gacacgatct cgcctcgccc gagcccagcc tcgggcaagg gcggccgacc ccgaggattc    180
```

```
acgtctcgcc cgagggcccc ctcaagcgac gggcacacct tcggctcgcc cgaggcccat    240
tcttcgccga gaagcaacct tggccagatc gccacaccga ccgaccgtat cgcaggagca    300
tttaatgcga ggatcgcctg acaccttatc ctgacgcgcg ctcttcagtc gacagagccg    360
aagtgaccgc aatcacttcg ccgctccact gaccgacctg acaagaagac agcgccgcct    420
gcgtcgctcc gactgctgtg ccactcgaca gagtgaggct gacagcagcc aagtccggcc    480
tcgggcgcca taggaagctc cgcctcgccc gaccctaggg ctcggactcg gcctcggctc    540
cggaagacga cgaactacgc ttcgcccgac cccagggctt ggactcagcc tcggctccgg    600
aagacgacga attccgcctc gcccgacccc agggctcgga ctcggcctcg gctccagaag    660
acgacgaact ccgcctcgcc cgacccagg gctcggactc agcctcggct ccggaagacg    720
acgaactccg cctcgcccga ccccagggct cggactcagc tcggcctca gacgatggtc    780 tccgcctcgc ccgacccggg gctcggactc ga                                  812
```

<210> SEQ ID NO 31
<211> LENGTH: 335
<212> TYPE: DNA
<213> ORGANISM: Artificial Sequence
<220> FEATURE:
<223> OTHER INFORMATION: Represents part of PHI8999A insert sequence - fragment of Cry1F gene

<400> SEQUENCE: 31

```
cctttctatc ggaccttgtc agatcctgtc ttcgtccgag gaggctttgg caatcctcac     60
tatgtactcg gtcttagggg agtggccttt caacaaactg gtacgaatca cccccgcaca    120
ttcaggaact ccgggaccat tgactctcta gatgagatac cacctcaaga caacagcggc    180
gcaccttgga atgactactc ccatgtgctg aatcatgtta cctttgtgcg ctggccaggt    240
gagatctcag gttccgactc atggagagca ccaatgttct cttggacgca tcgtagcgct    300 accccccacaa acaccattga tccagagaga atcac                              335
```

<210> SEQ ID NO 32
<211> LENGTH: 321
<212> TYPE: DNA
<213> ORGANISM: Zea mays
<220> FEATURE:
<221> NAME/KEY: misc_feature
<222> LOCATION: (0)...(0)
<223> OTHER INFORMATION: Fragment of maize chloroplast rpoC2 gene

<400> SEQUENCE: 32

```
tcattcttca agaactgcat atcttgccga gatcctcatc cctaaaggta cttgacaata     60
gtattattgg agtcgataca caactcacaa aaaatacaag aagtcgacta ggtggattgg    120
tccgagtgaa gagaaaaaaa agccatacag aactcaaaat cttttccgga gatattcatt    180
ttcctgaaga ggcggataag atattaggtg gcagtttgat accaccagaa agagaaaaaa    240
aagattctaa ggaatcaaaa aaaggaaaa attgggttta tgttcaacgg aaaaaatttc    300
tcaaaagcaa ggaaaagtat t                                              321
```

<210> SEQ ID NO 33
<211> LENGTH: 17
<212> TYPE: DNA
<213> ORGANISM: Artificial Sequence
<220> FEATURE:
<223> OTHER INFORMATION: Represents part of PHI8999A insert sequence-fragment of ubiZM1(2) promoter; also a fragment of the maize chloroplast trnI gene

<400> SEQUENCE: 33

```
gtggctattt atctatc                                                    17

<210> SEQ ID NO 34
<211> LENGTH: 201
<212> TYPE: DNA
<213> ORGANISM: Artificial Sequence
<220> FEATURE:
<223> OTHER INFORMATION: Represents part of PHI8999A insert
      sequence-fragment of pat gene

<400> SEQUENCE: 34
gcagctgata tggccgcggt ttgtgatatc gttaaccatt acattgagac gtctacagtg    60
aactttagga cagagccaca acaccacaa gagtggattg atgatctaga gaggttgcaa    120
gatagatacc cttggttggt tgctgaggtt gagggtgttg tggctggtat tgcttacgct    180
gggccctgga aggctaggaa c                                               201

<210> SEQ ID NO 35
<211> LENGTH: 138
<212> TYPE: DNA
<213> ORGANISM: Artificial Sequence
<220> FEATURE:
<223> OTHER INFORMATION: Represents part of PHI8999A insert
      sequence-fragment of pat gene (complement)

<400> SEQUENCE: 35
cctcaacctc agcaaccaac caatggtatc tatcttgcaa cctctctaga tcatcaatcc    60
actcttgtgg tgtttgtggc tctgtcctaa agttcactgt agacgtctca atgtaatggt   120
taacgatatc acaaaccg                                                  138

<210> SEQ ID NO 36
<211> LENGTH: 15
<212> TYPE: DNA
<213> ORGANISM: Artificial Sequence
<220> FEATURE:
<223> OTHER INFORMATION: Represents part of PHI8999A insert
      sequence-fragment of cry1F gene (complement)

<400> SEQUENCE: 36
agagaagagg gatct                                                      15

<210> SEQ ID NO 37
<211> LENGTH: 118
<212> TYPE: DNA
<213> ORGANISM: Artificial Sequence
<220> FEATURE:
<223> OTHER INFORMATION: Represents part of PHI8999A insert
      sequence-fragment of polylinker

<400> SEQUENCE: 37
cgaagcttcg gccggggccc atcgatatcc gcgggcatgc ctgcagtgca gcgtgacccg    60
gtcgtgcccc tctctagaga taatgagcat tgcatgtcta agttataaaa aattacca     118

<210> SEQ ID NO 38
<211> LENGTH: 550
<212> TYPE: DNA
<213> ORGANISM: Artificial Sequence
<220> FEATURE:
<223> OTHER INFORMATION: Represents part of PHI8999A insert
      sequence-fragment of ORF25 terminator (complement)

<400> SEQUENCE: 38
ctcactccgc ttgatcttgg caaagatatt tgacgcattt attagtatgt gttaattttc    60
```

-continued

```
atttgcagtg cagtattttc tattcgatct ttatgtaatt cgttacaatt aataaatatt      120
caaatcagat tattgactgt catttgtatc aaatcgtgtt taatggatat ttttattata      180
atattgatga tatctcaatc aaaacgtaga taataataat atttatttaa tatttttgcg      240
tcgcacagtg aaaatctata tgagattaca aaataccgac aacattattt aagaaacata     300
gacattaacc ctgagactgt tggacatcaa cgggtagatt ccttcatgca tagcacctca     360
ttcttgggga caaaagcacg gtttggccgt tccattgctg cacgaacgag ctttgctata      420
tcctcgggtt ggatcatctc atcaggtcca atcaaatttg tccaagaact catgttagtc    480
gcaacgaaac cggggcatat gtcgggtatc tcgagctcgc gaaagcttgg ctgcaggtcg    540
acggatcctt                                                            550
```

<210> SEQ ID NO 39
<211> LENGTH: 128
<212> TYPE: DNA
<213> ORGANISM: Zea mays
<220> FEATURE:
<221> NAME/KEY: misc_feature
<222> LOCATION: (0)...(0)
<223> OTHER INFORMATION: Fragment of maize chloroplast rps12 rRNA gene
      (complement)

<400> SEQUENCE: 39

```
caacaaaagg gtacctgtac ccgaaaccga cacaggtggg taggtagaga atacctaggg     60
gcgcgagaca actctctcta aggaactcgg caaaatagcc ccgtaacttc gggagaaggg   120
gtgccccc                                                              128
```

<210> SEQ ID NO 40
<211> LENGTH: 392
<212> TYPE: DNA
<213> ORGANISM: Zea mays
<220> FEATURE:
<221> NAME/KEY: misc_feature
<222> LOCATION: (0)...(0)
<223> OTHER INFORMATION: Fragment of maize chloroplast genome

<400> SEQUENCE: 40

```
ctaacaataa acgaatacgg tttatgtatg gattccggta aaataccggt actcgatttc     60
ataagagtcg aataggaagt taagatgagg gtggtatcat cataaaaatg gagtagtatc   120
ctaaattata ctaatccacg tatgatatgt atgcctttcc ttatcaaccg gaagtagtgc   180
aaaaaaaatt ctatactgca ctgctctctt tttactgaga aatgcaaaaa aataaaagtg    240
aagtaagggt gccccataga tatttgatct tgcctcctgt ccccccccc cttttttcat    300 caaaaatttc catgaaaaaa gaaagatga atttgtccat tcattgaacc ctagttcggg    360
actgacgggg ctcgaacccg cagcttccgc ct                                   392
```

<210> SEQ ID NO 41
<211> LENGTH: 188
<212> TYPE: DNA
<213> ORGANISM: Artificial Sequence
<220> FEATURE:
<223> OTHER INFORMATION: Represents part of PHI8999A insert
      sequence-fragment of pat gene (complement)

<400> SEQUENCE: 41

```
gttcctagcc ttccagggcc cagcgtaagc aataccagcc acagcaccct caacctcagc    60
aaccaaccaa gggtatctat cttgcaacct ctctagatca tcaatccact cttgtggtgt  120
ttgtggctct gtcctaaagt tcactgtaga cgtctcaatg taatggttaa cgatatcaca   180
```

```
aaccgcgg                                                              188
```

<210> SEQ ID NO 42
<211> LENGTH: 81
<212> TYPE: DNA
<213> ORGANISM: Zea mays
<220> FEATURE:
<221> NAME/KEY: misc_feature
<222> LOCATION: (0)...(0)
<223> OTHER INFORMATION: Fragment of maize chloroplast ORF241
      (complement)

<400> SEQUENCE: 42

```
cacaagaacg aaagcacctt ttcattcttt catatactag gggtttttac ttggaaaaga     60
caatgttcca tactaaagga t                                               81
```

<210> SEQ ID NO 43
<211> LENGTH: 254
<212> TYPE: DNA
<213> ORGANISM: Zea mays

<400> SEQUENCE: 43

```
agctgcagaa gccgccaccg tcttgaggac cttccgggga gccagaccgg tcgaaccgtg     60
cctccacttg ctaaggagaa agggaaaatc agggccagga catacgaagg aggagccaga   120
acgaagatat cctaagatac ttactcgctc cgggccatga tcaatcatgc ctgtggggag   180
gtctctcgca cctcgatcca tgaaggtacc accgaggtct gccccgccgc cggcttcggt   240
accgtcctcg cctt                                                     254
```

<210> SEQ ID NO 44
<211> LENGTH: 749
<212> TYPE: DNA
<213> ORGANISM: Zea mays

<400> SEQUENCE: 44

```
gggcgcccga ggcacccggg ggatggactg cccaggcgca gccacgacga cccaaggatc     60
accctcctgc gcagtcggca cgagcaatag ttctcgggga acaggcagct tggcctgact   120
ccccggggtc acctcaacta cctcggccga ggggtcaagt accccctcag tccgcccccg   180
ctcttcggac cgggacgggg cccggatacc gacggcacca gcccgctcgg                     240
gggctggctt gacgacccct ggcccagcct cagatctggg ctgaggccga ggcaggcggc   300
catgtcgtcg tcttcatcat cgtcttcatc atcgtcgtcg tcatcaggcg tctccggcga   360
cggctcccct gggagcccct ccctctcctg ccgacgacga agcctttcca aggcatcccg   420
agcccacgtc cgctcgtggg cccgagcctt ctttgcgtcc ttcttctcct tcctcttctc   480
cgcggtgacc ctccgcgcag ctcggtccac cgcatcctcc gggactggtg gcagggaagg   540
cttgtgatgc cctacctcct ggagacagac gaaaagtctc agctatgaga accgagggca   600
atctgacgca agaaggaaga aggagcggat actcaccaga gacacgcacc cgcgatcggg   660
acgcattaag ggctgggaaa aagtgccggc ctctaatttc gctaccgtgc cgtccaccca   720
cctgtggagg tcatcgatgg gaagggggaa                                     749
```

<210> SEQ ID NO 45
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 3 and 4

```
<400> SEQUENCE: 45
tcggactcga cctttctatc                                          20

<210> SEQ ID NO 46
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 4 and 5

<400> SEQUENCE: 46
agagaatcac tcattcttca                                          20

<210> SEQ ID NO 47
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 5 and 6

<400> SEQUENCE: 47
gaaaagtatt gtggctattt                                          20

<210> SEQ ID NO 48
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 6 and 7a

<400> SEQUENCE: 48
tctcaaggcc gcagctgata                                          20

<210> SEQ ID NO 49
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 7a and 7b

<400> SEQUENCE: 49
ggctaggaac cctcaacctc                                          20

<210> SEQ ID NO 50
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 7b and 7c

<400> SEQUENCE: 50
tcacaaaccg agagaagagg                                          20

<210> SEQ ID NO 51
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 7c and 8

<400> SEQUENCE: 51
```
agagggatct cgaagcttcg                    20

<210> SEQ ID NO 52
<211> LENGTH: 20
<212> TYPE: DNA
<213> ORGANISM: Artificial Sequence
<220> FEATURE:
<223> OTHER INFORMATION: Biolistic transformation event 5' flanking
      sequence; junction between regions 8 and 9

<400> SEQUENCE: 52
aaaattacca caactggaag                    20

<210> SEQ ID NO 53
<211> LENGTH: 20
<212> TYPE: DNA
<213> ORGANISM: Artificial Sequence
<220> FEATURE:
<223> OTHER INFORMATION: Biolistic transformation event 3' flanking
      sequence; junction between regions 9 and 10

<400> SEQUENCE: 53
agctatgttt ctcactccgc                    20

<210> SEQ ID NO 54
<211> LENGTH: 20
<212> TYPE: DNA
<213> ORGANISM: Artificial Sequence
<220> FEATURE:
<223> OTHER INFORMATION: Biolistic transformation event 3' flanking
      sequence; junction between regions 10 and 11

<400> SEQUENCE: 54
acggatcctt caacaaaagg                    20

<210> SEQ ID NO 55
<211> LENGTH: 20
<212> TYPE: DNA
<213> ORGANISM: Artificial Sequence
<220> FEATURE:
<223> OTHER INFORMATION: Biolistic transformation event 3' flanking
      sequence; junction between regions 11 and 12

<400> SEQUENCE: 55 gtgcccccg ctaacaataa                     20

<210> SEQ ID NO 56
<211> LENGTH: 20
<212> TYPE: DNA
<213> ORGANISM: Artificial Sequence
<220> FEATURE:
<223> OTHER INFORMATION: Biolistic transformation event 3' flanking
      sequence; junction between regions 12 and 13

<400> SEQUENCE: 56
gcttccgcct gttcctagcc                    20

<210> SEQ ID NO 57
<211> LENGTH: 20
<212> TYPE: DNA
<213> ORGANISM: Artificial Sequence
<220> FEATURE:
<223> OTHER INFORMATION: Biolistic transformation event 3' flanking
      sequence; junction between regions 13 and 14

<400> SEQUENCE: 57
aaaccgcgga acacaagaac                    20

CORN EVENT TC1507 AND METHODS FOR DETECTION THEREOF

CROSS-REFERENCE TO RELATED APPLICATIONS

This application is a Continuation of U.S. Ser. No. 11/774,236, now U.S. Pat. No. 7,514,544, filed Jul. 6, 2007, which is a divisional of U.S. Ser. No. 10/837,105, now U.S. Pat. No. 7,288,643, filed Apr. 30, 2004, which claims priority to U.S. Provisional Application No. 60/467,772, filed May 2, 2003.

FIELD OF THE INVENTION

The present invention relates to the field of plant molecular biology, specifically the invention relates to a DNA construct for conferring insect resistance to a plant. The invention more specifically relates to an insect resistant corn plant TC1507 and to assays for detecting the presence of corn plant TC1507 DNA in a sample and compositions thereof.

BACKGROUND OF THE INVENTION

This invention relates to the insect resistant corn (*Zea mays*) plant TC1507, also referred to as maize line TC1507 or maize event TC1507, and to the DNA plant expression construct of corn plant TC1507 and the detection of the transgene/flanking insertion region in corn plant TC1507 and progeny thereof.

Corn is an important crop and is a primary food source in many areas of the world. Damage caused by insect pests is a major factor in the loss of the world's corn crops, despite the use of protective measures such as chemical pesticides. In view of this, insect resistance has been genetically engineered into crops such as corn in order to control insect damage and to reduce the need for traditional chemical pesticides. One group of genes which have been utilized for the production of transgenic insect resistant crops are the delta-endotoxins from *Bacillus thuringiensis* (B.t.). Delta-endotoxins have been successfully expressed in crop plants such as cotton, potatoes, rice, sunflower, as well as corn, and have proven to provide excellent control over insect pests. (Perlak, F. J et al. (1990) *Bio/Technology* 8, 939-943; Perlak, F. J. et al. (1993) *Plant Mol. Biol.* 22:313-321; Fujimoto H. et al. (1993) *Bio/Technology* 11: 1151-1155; Tu et al. (2000) *Nature Biotechnology* 18:1101-1104; PCT publication number WO 01/13731; and Bing J W et al. (2000) Efficacy of Cry1F Transgenic Maize, 14$^{th}$ Biennial International Plant Resistance to Insects Workshop, Fort Collins, Colo.).

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgene by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in U.S. Pat. No. 6,395,485 for the detection of elite event GAT-ZM1. Accordingly, it would be desirable to have a simple and discriminative method for the identification of event TC1507.

SUMMARY OF THE INVENTION

This invention relates preferably to methods for producing and selecting an insect resistant monocot crop plant. More specifically, a DNA construct is provided that when expressed in plant cells and plants confers resistance to insects. According to one aspect of the invention, a DNA construct, capable of introduction into and replication in a host cell, is provided that when expressed in plant cells and plants confers insect resistance to the plant cells and plants. The DNA construct is comprised of a DNA molecule named PHI8999A and it includes two transgene expression cassettes. The first expression cassette comprises a DNA molecule which includes the promoter, 5' untranslated exon, and first intron of the maize ubiquitin (Ubi-1) gene (Christensen et al. (1992) *Plant Mol. Biol.* 18:675-689 and Christensen and Quail (1996) *Transgenic Res.* 5:213-218) operably connected to a DNA molecule encoding a B.t. δ-endotoxin identified as Cry1F (U.S. Pat. Nos. 5,188,960 and 6,218,188) operably connected to a DNA molecule comprising a 3' ORF25 transcriptional terminator isolated from *Agrobacterium tumefaciens* (Barker et al. (1983) *Plant Mol. Biol.* 2:335-350). The second transgene expression cassette of the DNA construct comprises a DNA molecule of the cauliflower mosaic virus (CaMV) 35S promoter (Odell J. T. et al. (1985) *Nature* 313: 810-812; Mitsuhara et al. (1996) *Plant Cell Physiol.* 37: 49-59) operably connected to a DNA molecule encoding a phosphinothricin acetyltransferase (PAT) gene (Wohlleben W. et al. (1988)

*Gene* 70: 25-37) operably connected to a DNA molecule comprising a 3' transcriptional terminator from (CaMV) 35S (see Mitsuhara et al. (1996) *Plant Cell Physiol.* 37: 49-59). Plants containing the DNA construct are also provided.

According to another aspect of the invention, compositions and methods are provided for identifying a novel corn plant designated TC1507, which methods are based on primers or probes which specifically recognize the 5' and/or 3' flanking sequence of TC1507. DNA molecules are provided that comprise primer sequences that when utilized in a PCR reaction will produce amplicons unique to the transgenic event TC1507. These molecules may be selected from the group consisting of:

```
                                           (SEQ ID NO: 1)
    5'-GTAGTACTATAGATTATATTATTCGTAGAG-3';

(SEQ ID NO: 2)
    5'-GCCATACAGAACTCAAAATCTTTTCCGGAG-3';

(SEQ ID NO: 23)
    5'-CTTCAAACAAGTGTGACAAA-3';

(SEQ ID NO: 3)
    5'-TGTGGTGTTTGTGGCTCTGTCCTAA-3';

(SEQ ID NO: 4)
    5'-AGCACCTTTTCATTCTTTCATATAC-3';

(SEQ ID NO: 5)
    5'-GACCTCCCCA CAGGCATGAT TGATC-3';
``` and complements thereof. The corn plant and seed comprising these molecules is an aspect of this invention. Further, kits utilizing these primer sequences for the identification of the TC1507 event are provided.

An additional aspect of the invention relates to the specific flanking sequences of TC1507 described herein, which can be used to develop specific identification methods for TC1507 in biological samples. More particularly, the invention relates to the 5' and/or 3' flanking regions of TC1507, SEQ ID NO:21 and SEQ ID NO:22, respectively, which can be used for the development of specific primers and probes. The invention further relates to identification methods for the presence of TC1507 in biological samples based on the use of such specific primers or probes.

According to another aspect of the invention, methods of detecting the presence of DNA corresponding to the corn event TC1507 in a sample are provided. Such methods comprise: (a) contacting the sample comprising DNA with a DNA primer set, that when used in a nucleic acid amplification reaction with genomic DNA extracted from corn event TC1507 produces an amplicon that is diagnostic for corn event TC1507; (b) performing a nucleic acid amplification reaction, thereby producing the amplicon; and (c) detecting the amplicon.

DNA molecules that comprise the novel transgene/flanking insertion region, SEQ ID NO: 26 and SEQ ID NO: 27 and are homologous or complementary to SEQ ID NO: 26 and SEQ ID NO: 27 are an aspect of this invention.

DNA sequences that comprise the novel transgene/flanking insertion region, SEQ ID NO:26 are an aspect of this invention. DNA sequences that comprise a sufficient length of polynucleotides of transgene insert sequence and a sufficient length of polynucleotides of maize genomic and/or flanking sequence from maize plant TC1507 of SEQ ID NO:26 that are useful as primer sequences for the production of an amplicon product diagnostic for maize plant TC1507 are included.

In addition, DNA sequences that comprise the novel transgene/flanking insertion region, SEQ ID NO:27 are provided. DNA sequences that comprise a sufficient length of polynucleotides of transgene insert sequence and a sufficient length of polynucleotides of maize genomic and/or flanking sequence from maize plant TC1507 of SEQ ID NO:27 that are useful as primer sequences for the production of an amplicon product diagnostic for maize plant TC1507 are included.

According to another aspect of the invention, the DNA sequences that comprise at least 11 or more nucleotides of the transgene portion of the DNA sequence of SEQ ID NO:26 or complements thereof, and a similar length of 5' flanking maize DNA sequence of SEQ ID NO:26 or complements thereof are useful as DNA primers in DNA amplification methods. The amplicons produced using these primers are diagnostic for maize event TC1507. Therefore, the invention also includes the amplicons produced by DNA primers homologous or complementary to SEQ ID NO:26.

According to another aspect of the invention, the DNA sequences that comprise at least 11 or more nucleotides of the transgene portion of the DNA sequence of SEQ ID NO:27 or complements thereof, and a similar length of 3' flanking maize DNA sequence of SEQ ID NO:27 or complements thereof are useful as DNA primers in DNA amplification methods. The amplicons produced using these primers are diagnostic for maize event TC1507. Therefore, the invention also includes the amplicons produced by DNA primers homologous or complementary to SEQ ID NO:27.

More specifically, a pair of DNA molecules comprising a DNA primer set, wherein the DNA molecules are identified as SEQ ID NO: 1 or complements thereof and SEQ ID NO: 2 or complements thereof; SEQ ID NO: 2 or complements thereof and SEQ ID NO: 23 or complements thereof; SEQ ID NO: 3 or complements thereof and SEQ ID NO: 5 or complements thereof; SEQ ID NO: 4 or complements thereof and SEQ ID NO: 5 or complements thereof are aspects of the invention.

Further aspects of the invention include the amplicon comprising the DNA molecules of SEQ ID NO: 1 and SEQ ID NO: 2; the amplicon comprising the DNA molecules of SEQ ID NO: 2 and SEQ ID NO: 23; the amplicon comprising the DNA molecules of SEQ ID NO: 3 and SEQ ID NO: 5; and the amplicon comprising the DNA molecules of SEQ ID NO: 4 and SEQ ID NO: 5.

According to another aspect of the invention, methods of detecting the presence of a DNA molecule corresponding to the TC1507 event in a sample, such methods comprising: (a) contacting the sample comprising DNA extracted from a corn plant with a DNA probe, molecule that hybridizes under stringent hybridization conditions with DNA extracted from corn event TC1507 and does not hybridize under the stringent hybridization conditions with a control corn plant DNA; (b) subjecting the sample and probe to stringent hybridization conditions; and (c) detecting hybridization of the probe to the DNA. More specifically, a method for detecting the presence of a DNA molecule corresponding to the TC1507 event in a sample, such methods, consisting of (a) contacting the sample comprising DNA extracted from a corn plant with a DNA probe molecule that consists of sequences that are unique to the event, e.g. junction sequences, wherein said DNA probe molecule hybridizes under stringent hybridization conditions with DNA extracted from corn event TC1507 and does not hybridize under the stringent hybridization conditions with a control corn plant DNA; (b) subjecting the sample and probe to stringent hybridization conditions; and (c) detecting hybridization of the probe to the DNA.

In addition, a kit and methods for identifying event TC1507 in a biological sample which detects a TC1507 specific region within SEQ ID NO: 24 are provided.

DNA molecules are provided that comprise at least one junction sequence of TC1507 selected from the group consisting of SEQ ID NO:45, 46, 47, 48, 49, 50, 51, 52, 53, 54, 55, 56 and 57 and complements thereof; wherein a junction sequence spans the junction between heterologous DNA inserted into the genome and the DNA from the corn cell flanking the insertion site, i.e. flanking DNA, and is diagnostic for the TC1507 event.

According to another aspect of the invention, methods of producing an insect resistant corn plant that comprise the steps of: (a) sexually crossing a first parental corn line comprising the expression cassettes of the present invention, which confers resistance to insects, and a second parental corn line that lacks insect resistance, thereby producing a plurality of progeny plants; and (b) selecting a progeny plant that is insect resistant. Such methods may optionally comprise the further step of back-crossing the progeny plant to the second parental corn line to producing a true-breeding corn plant that is insect resistant.

The present invention provides a method of producing a corn plant that is resistant to insects comprising transforming a corn cell with the DNA construct PHI8999A (SEQ ID NO:25), growing the transformed corn cell into a corn plant, selecting the corn plant that shows resistance to insects, and further growing the corn plant into a fertile corn plant. The fertile corn plant can be self pollinated or crossed with compatible corn varieties to produce insect resistant progeny.

The invention further relates to a DNA detection kit for identifying maize event TC1507 in biological samples. Preferably the kit of the invention comprises a first primer which specifically recognizes the 5' or 3' flanking region of TC1507, and a second primer which specifically recognizes a sequence within the foreign DNA of TC1507, or within the flanking DNA, for use in a PCR identification protocol. The invention also relates to a kit for identifying event TC1507 in biological samples, which kit comprises a specific probe having a sequence which corresponds or is complementary to, a sequence having between 80% and 100% sequence identity with a specific region of event TC1507. Preferably the sequence of the probe corresponds to a specific region comprising part of the 5' or 3' flanking region of event TC1507.

The methods and kits encompassed by the present invention can be used for different purposes such as, but not limited to the following: to identify event TC1507 in plants, plant material or in products such as, but not limited to, food or feed products (fresh or processed) comprising, or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality of plant material comprising maize event TC1507. The kits may also contain the reagents and materials necessary for the performance of the detection method.

This invention further relates to the TC1507 corn plant or its parts, including, but not limited to, pollen, ovules, vegetative cells, the nuclei of pollen cells, and the nuclei of egg cells of the corn plant TC1507 and the progeny derived thereof. The corn plant and seed TC1507 from which the DNA primer molecules of the present invention provide a specific amplicon product is an aspect of the invention.

The foregoing and other aspects of the invention will become more apparent from the following detailed description and accompanying drawing.

BRIEF DESCRIPTION OF THE DRAWINGS

FIG. 1. Linear map showing the transgenic insert PHI8999A, as well as the sequences flanking the transgenic insert.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, $5^{th}$ edition, Springer-Verlag; New York, 1991; and Lewin, *Genes V*, Oxford University Press: New York, 1994. The nomenclature for DNA bases as set forth at 37 CFR 1.822 is used.

As used herein, the term "comprising" means "including but not limited to".

As used herein, the term "corn" means *Zea mays* or maize and includes all plant varieties that can be bred with corn, including wild maize species.

As used herein, the term "TC1507 specific" refers to a nucleotide sequence which is suitable for discriminatively identifying event TC1507 in plants, plant material, or in products such as, but not limited to, food or feed products (fresh or processed) comprising, or derived from plant material.

As used herein, the terms "insect resistant" and "impacting insect pests" refers to effecting changes in insect feeding, growth, and/or behavior at any stage of development, including but not limited to: killing the insect; retarding growth; preventing reproductive capability; and the like.

As used herein, the terms "pesticidal activity" and "insecticidal activity" are used synonymously to refer to activity of an organism or a substance (such as, for example, a protein) that can be measured by numerous parameters including, but not limited to, pest mortality, pest weight loss, pest attraction, pest repellency, and other behavioral and physical changes of a pest after feeding on and/or exposure to the organism or substance for an appropriate length of time. For example "pesticidal proteins" are proteins that display pesticidal activity by themselves or in combination with other proteins.

"Coding sequence" refers to a nucleotide sequence that codes for a specific amino acid sequence. As used herein, the terms "encoding" or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. "Foreign" refers to material not normally found in the location of interest. Thus "foreign DNA" may comprise both recombinant DNA as well as newly introduced, rearranged DNA of the plant. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. The site in the plant genome where a recombinant DNA has been inserted may be referred to as the "insertion site" or "target site".

As used herein, "insert DNA" refers to the heterologous DNA within the expression cassettes used to transform the plant material while "flanking DNA" can exist of either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20 base pair, preferably at least 50 base pair, and up to 5000 base pair which is located either immediately upstream of and contiguous with or immediately downstream of and contiguous with the original foreign insert DNA molecule. Transformation procedures leading to random integration of the foreign DNA will result in transformants containing different flanking regions characteristic and unique for each transformant. When recombinant DNA is introduced into a plant through traditional crossing, its flanking regions will generally not be changed. Transformants will also contain unique junctions between a piece of heterologous insert DNA and genomic DNA, or 2 pieces of genomic DNA, or 2 pieces of heterologous DNA. A "junction" is a point where 2 specific DNA fragments join. For example, a junction exists where insert DNA joins flanking DNA. A junction point also exists in a transformed organism where 2 DNA fragments join together in a manner that is modified from that found in the native organism. "Junction DNA" refers to DNA that comprises a junction point.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

A "protein" or "polypeptide" is a chain of amino acids arranged in a specific order determined by the coding sequence in a polynucleotide encoding the polypeptide.

A DNA construct is an assembly of DNA molecules linked together that provide one or more expression cassettes. The DNA construct may be a plasmid that is enabled for self replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette. The expression cassette contained within a DNA construct comprise the necessary genetic elements to provide transcription of a messenger RNA. The expression cassette can be designed to express in prokaryote cells or eukaryotic cells. Expression cassettes of the present invention are designed to express most preferably in plant cells.

The DNA molecules of the invention are provided in expression cassettes for expression in an organism of interest. The cassette will include 5' and 3' regulatory sequences operably linked to a coding sequence of the invention. "Operably linked" means that the nucleic acid sequences being linked are contiguous and, where necessary to join two protein coding regions, contiguous and in the same reading frame. Operably linked is intended to indicate a functional linkage between a promoter and a second sequence, wherein the promoter sequence initiates and mediates transcription of the DNA sequence corresponding to the second sequence. The cassette may additionally contain at least one additional gene to be cotransformed into the organism. Alternatively, the additional gene(s) can be provided on multiple expression cassettes or multiple DNA constructs.

The expression cassette will include in the 5' to 3' direction of transcription: a transcriptional and translational initiation region, a coding region, and a transcriptional and translational termination region functional in the organism serving as a host. The transcriptional initiation region (i.e., the promoter) may be native or analogous, or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

An insect resistant TC1507 corn plant can be bred by first sexually crossing a first parental corn plant consisting of a corn plant grown from the transgenic TC1507 corn plant and progeny thereof derived from transformation with the expression cassettes of the present invention that confers insect resistance, and a second parental corn plant that lacks insect resistance, thereby producing a plurality of first progeny plants; and then selecting a first progeny plant that is resistant to insects; and selfing the first progeny plant, thereby producing a plurality of second progeny plants; and then selecting from the second progeny plants an insect resistant plant. These steps can further include the back-crossing of the first insect resistant progeny plant or the second insect resistant progeny plant to the second parental corn plant or a third parental corn plant, thereby producing a corn plant that is resistant to insects.

As used herein, the term "plant" includes reference to whole plants, plant organs (e.g., leaves, stems, roots, etc.), seeds, plant cells, and progeny of same. Parts of transgenic plants understood to be within the scope of the invention comprise, for example, plant cells, protoplasts, tissues, callus, embryos as well as flowers, stems, fruits, leaves, and roots originating in transgenic plants or their progeny previously transformed with a DNA molecule of the invention and therefore consisting at least in part of transgenic cells, are also an aspect of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Additional transformation methods are disclosed below.

Thus, isolated polynucleotides of the present invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of isolated DNA from corn event TC1507 whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence specifically in the hybridization conditions or reaction conditions determined by the operator. This length may be of any length that is of sufficient length to be useful in a detection method of choice. Generally, 11 nucleotides or more in length, preferably 18 nucleotides or more, and more preferably 22 nucleotides or more, are used. Such probes and primers hybridize specifically to a target sequence under high stringency hybridization conditions. Preferably, probes and primers according to the present invention have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and not be used in an amplification process.

Specific primers can be used to amplify an integration fragment to produce an amplicon that can be used as a "specific probe" for identifying event TC1507 in biological samples. When the probe is hybridized with the nucleic acids of a biological sample under conditions which allow for the binding of the probe to the sample, this binding can be detected and thus allow for an indication of the presence of event TC1507 in the biological sample. Such identification of a bound probe has been described in the art. The specific probe is preferably a sequence which, under optimized conditions, hybridizes specifically to a region within the 5' or 3' flanking region of the event and preferably also comprises a part of the foreign DNA contiguous therewith. Preferably the specific probe comprises a sequence of at least 80%, preferably between 80 and 85%, more preferably between 85 and 90%, especially preferably between 90 and 95%, and most preferably between 95 and 100% identical (or complementary) to a specific region of the event.

Methods for preparing and using probes and primers are described, for example, in *Molecular Cloning: A Laboratory Manual*, $2^{nd}$ ed., vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5, ©1991, Whitehead Institute for Biomedical Research, Cambridge, Mass.). Additionally, the sequence can be visually scanned and primers manually identified using guidelines known to one of skill in the art.

A "kit" as used herein refers to a set of reagents for the purpose of performing the method of the invention, more particularly, the identification of the event TC1507 in biological samples. The kit of the invention can be used, and its components can be specifically adjusted, for purposes of quality control (e.g. purity of seed lots), detection of event TC1507 in plant material, or material comprising or derived from plant material, such as but not limited to food or feed products. "Plant material" as used herein refers to material which is obtained or derived from a plant.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

In hybridization reactions, specificity is typically the function of post-hybridization washes, the critical factors being the ionic strength and temperature of the final wash solution. The thermal melting point (Tm) is the temperature (under defined ionic strength and pH) at which 50% of a complementary target sequence hybridizes to a perfectly matched probe. For DNA-DNA hybrids, the Tm can be approximated from the equation of Meinkoth and Wahl (1984) *Anal. Biochem.* 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm.

Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

As used herein, a substantially homologous sequence is a nucleic acid molecule that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of a destabilizing agent such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. In a preferred embodiment, a nucleic acid of the present invention will specifically hybridize to one or more of the nucleic acid molecules unique to the TC1507 event or complements thereof or fragments of either under moderately stringent conditions.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (version 3.0, copyright 1997); and GAP, BESTFIT, BLAST, FASTA, and TFASTA in the Wisconsin Genetics Software Package, Version 10 (available from Accelrys, 9685 Scranton Road, San Diego, Calif. 92121, USA). Alignments using these programs can be performed using the default parameters.

The CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994). The ALIGN and the ALIGN PLUS programs are based on the algorithm of Myers and Miller (1988) supra. The BLAST programs of Altschul et al. (1990) *J. Mol. Biol.* 215:403 are based on the algorithm of Karlin and Altschul (1990) supra. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Alignment may also be performed manually by inspection.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Institutes of Health National Center for Biotechnology Information website.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether a corn plant resulting from a sexual cross contains transgenic event genomic DNA from the corn plant of the present invention, DNA extracted from the corn plant tissue sample may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA. Alternatively, the second primer may be derived from the flanking sequence. The amplicon is of a length and has a sequence that is also diagnostic for the event. The amplicon may range in length from the combined length of the primer pairs plus one nucleotide base pair to any length of amplicon producible by a DNA amplification protocol. Alternatively, primer pairs can be derived from flanking sequence on both sides of the inserted DNA so as to produce an amplicon that includes the entire insert nucleotide sequence of the PHI8999A expression construct, see FIG. 1, approximately 6.2 Kb in size. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic press, San Diego, 1990. PCR amplification methods have been developed to amplify up to 22 Kb of genomic DNA and up to 42 Kb of bacteriophage DNA (Cheng et al., *Proc. Natl. Acad. Sci. USA* 91:5695-5699, 1994). These methods as well as other methods known in the art of DNA amplification may be used in the practice of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al. *Nucleic Acid Res.* 22:4167-4175, 1994) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge (*Innov. Pharma. Tech.* 00: 18-24, 2000). In this method an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al., (*Genome Res.* 9:492-498, 1999) is a method that can be used to detect an amplicon of the present invention. Using this method an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. (*Nature Biotech.* 14:303-308, 1996). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXAMPLES

Example 1

Transformation of Maize by Particle Bombardment and Regeneration of Transgenic Plants Containing the Cry1F Gene A DNA molecule of 6.2 Kb, designated PHI8999A (see FIG. 1 and SEQ ID NO:25), which includes a first transgene expression cassette comprising the promoter, 5' untranslated exon, and first intron of the maize ubiquitin (Ubi-1) gene (Christensen et al. (1992) Plant Mol. Biol. 18:675-689 and Christensen and Quail (1996) Transgenic Res. 5:213-218) operably connected to a DNA molecule encoding a *Bacillus thuringiensis* δ-endotoxin identified as Cry1F (U.S. Pat. Nos. 5,188,960 and 6,218,188) operably connected to a DNA molecule comprising a 3' ORF25 transcriptional terminator isolated from *Agrobacterium tumefaciens* (Barker et al. (1983) *Plant Mol. Biol.* 2:335-350), and a second transgene expression cassette comprising a DNA molecule of the cauliflower mosaic virus (CaMV) 35S promoter (Odell J. T. et al. (1985) *Nature* 313: 810-812; Mitsuhara et al. (1996) *Plant Cell Physiol.* 37:49-59) operably connected to a DNA molecule encoding the selectable marker, phosphinothricin acetyl-transferase (PAT) gene (Wohlleben W. et al. (1988) *Gene* 70:25-37) operably connected to a DNA molecule comprising a 3' transcriptional terminator from (CaMV) 35S (see Mitsuhara et al. (1996) *Plant Cell Physiol.* 37:49-59) was used to transform maize embryo tissue.

B.t. Cry1F maize plants were obtained by microprojectile bombardment using the Biolistics® PDS-1000He particle gun manufactured by Bio-Rad, Hercules, Calif.; essentially as described by Klein et al. (1987) *Nature*, UK 327(6117): 70-73. Immature embryos isolated from maize ears, harvested soon after pollination were cultured on callus initiation medium for several days. On the day of transformation, microscopic tungsten particles were coated with purified PHI8999A DNA (SEQ ID NO:25) and accelerated into the cultured embryos, where the insert DNA was incorporated into the cell chromosome. Only insert PHI8999A was used during transformation and no additional plasmid DNA was incorporated into the transformant. After bombardment, embryos were transferred to callus initiation medium containing glufosinate as the selection agent. Individual embryos were kept physically separate during culture, and the majority of explants died on the selective medium.

Those embryos that survived and produced healthy, glufosinate-resistant callus tissue were assigned unique identification codes representing putative transformation events, and continually transferred to fresh selection medium. Plants were regenerated from tissue derived from each unique event and transferred to the greenhouse. Leaf samples were taken for molecular analysis to verify the presence of the transgene by PCR and to confirm expression of the Cry1F protein by ELISA. Plants were then subjected to a whole plant bioassay using European corn borer insects. Positive plants were crossed with inbred lines to obtain seed from the initial transformed plants. A number of lines were evaluated in the field. The TC1507 event was selected from a population of independent transgenic events based on a superior combination of characteristics, including insect resistance and agronomic performance (see Bing J W et al. (2000) Efficacy of Cry1F Transgenic Maize, 14$^{th}$ Biennial International Plant Resistance to Insects Workshop, fort Collins, Colo., herein incorporated by reference).

Example 2

Identification of Nucleotides Comprising the Flanking Sequence 5' to the Transgenic Insert DNA in *Bacillus thuringiensis* Cry1F Maize Line TC1507

To identify a DNA fragment that included sequence 5' to the PHI8999A insert in event TC1507, Spe I restriction enzyme fragments from event TC1507 genomic DNA were size selected on agarose gels, purified, and screened by Southern analysis to confirm hybridization to a Cry1F probe. Following confirmation of hybridization and fragment size, the fragments of interest were cloned into a pBluescript II SK (+)™ cloning vector to prepare an enriched size selected plasmid based genomic DNA library. A probe homologous to a portion of the Cry1F gene was used to screen the plasmid library for positive clones. A positive clone was identified, purified by additional screening, and confirmed to result in a positive signal when hybridized to the Cry1F probe. Nearly 3 Kb of the Spe I fragment contained in the isolated positive clone was sequenced using a primer walking approach. To initiate the first sequencing run, a primer that binds to a known sequence in the cloning vector DNA was designed to sequence a portion of the DNA of interest. A second sequencing run over the same region using another primer oriented in the reverse direction provided second strand coverage. Primer walking was accomplished by repeatedly using sequence data from previous runs to design new primers that were then used to extend the next round of sequencing further into the DNA of interest until the flanking sequence 5' to the inserted transgenic DNA in maize event TC1507 was obtained. Specific sequence information is provided in Example 4.

Example 3

Confirmation of Flanking Sequence 5' to the B.t. Cry1F Maize Line TC1507 Insert

To confirm the 5' flanking sequence of the B.t. Cry1F maize line TC1507 insert, PCR primer pairs were designed to obtain overlapping PCR products extending from the 5' flanking region into the full-length PHI8999A transgenic insert. PCR products were successfully amplified from B.t. Cry1F maize line TC1507 genomic DNA, isolated, and sequenced for Region 1 through Region 6, shown in Table 1, and confirmed to match the previously determined sequence from the Spe I fragment, described in Example 2. However, the region from bp 2358 to bp 2829, immediately adjacent and 5' to the start of the full-length insert was recalcitrant to PCR amplification and appeared to be larger than the sequence obtained from the Spe I clone described above. The use of primer pairs flanking this region and the Advantage®-GC 2 Polymerase Mix (BD Biosciences Clontech, Palo Alto, Calif.) was successful in amplifying PCR products from B.t. Cry1F maize line TC1507 genomic DNA for sequencing. The amplification conditions used to produce amplicons with the Advantage®-GC 2 system are shown in Table 10. The DNA primer pairs used to confirm the sequence in the region from bp 2358 to 2829 are those listed in SEQ ID NO:1 and SEQ ID NO:2; and SEQ ID NO:2 and SEQ ID NO:23. Sequence from this region is described in Table 1 (Regions 7a, 7b, 7c, and 8).

Example 4

Event TC1507 5' Flanking Sequence. A Description of Each Region is Provided in Table 1

```
Region 1 (SEQ ID NO: 28) Maize genomic (no significant
homology)
    1   ACTAGTTTCC TAGCCCGCGT CGTGCCCCTA CCCCACCGAC GTTTATGGAA

51   GGTGCCATTC CACGGTTCTT CGTGGCCGCC CCTAAGGATG TAAATGGTCG

101   GTAAAATCCG GTAAATTTCC GGTACCGTTT ACCAGATTTT TCCAGCCGTT

151   TTCGGATTTA TCGGGATATA CAGAAAACGA GACGGAAACG GAATAGGTTT

201   TTTTTCGAAA ACGGTACGGT AAACGGTGAG ACAAACTTAC CGTCCGTTTT

251   CGTATTTCTC GGGAAACTCT GGTATATTCC CGTATTTGTC CCGTATTTTC

301   CCGACCCACG GACCTGCCAA TCAACCATCA GCCAGTCAGC CCATCCCCAC

351   AGCTATGGCC CATGGGGCCA TGTTGGCCAC ATGCCCACGC AACGCAAGGC

401   AGTAAGGCTG GCAGCCTGGC ACGCATTGAC GCATGTGGAC ACACACAGCC

451   GCCGCCTGTT CGTGTTTCTG TGCCGTTGTG CGAGACTGTG ACTGCGAGTG

501   GCGGAGTCGG CGAACGGCGA GGCGTCTCCG GAGTCTGGAC TGCGGCTGTG

551   GACAGCGACG CTGTGACGGC GACTCGGCGA AGCCCCAAGC TACCAAGCCC

601   CCAAGTCCCC ATCCATCTCT GCTTCTCTGG TCATCTCCTT CCCCTGGTCG

651   ATCTGCAGGC GCCAGACCG

Region 2 (SEQ ID NO: 29) Undescribed maize genomic sequence
(complement)
  670   G CCGAAGCATC ACGAAACGCA CTAAGACCTC

701   GAAGGAGTCA AACCACTCCT CCGAGGCCTC GGGGGCTACA CCCGGCGGGT

751   GCGCTCGCGC GCACCCACCG GAACAAAATG TAACCGAGAA AGGTCGGTCC

801   CCTTGCAAAA AAAGTGCGAC AAAAGCCTCC AAGCGAGTAT TAACACTCAC

851   TTTGAGGCTC GGGGGCTAC

Region 3 (SEQ ID NO: 30) Fragment of maize Huck-1
retrotransposon
  870   T GTCGGGGACC ATAATTAGGG GTACCCCCAA

901   GACTCCTAAT CTCAGCTGGT AACCCCCATC AGCACAAAGC TGCAAAGGCC
```

```
 951  TGATGGGTGC GATTAAGTCA AGGCTCGGTC CACTCAAGGG ACACGATCTC

1001  GCCTCGCCCG AGCCCAGCCT CGGGCAAGGG CGGCCGACCC CGAGGATTCA

1051  CGTCTCGCCC GAGGGCCCCC TCAAGCGACG GCACACCTT CGGCTCGCCC

1101  GAGGCCCATT CTTCGCCGAG AAGCAACCTT GGCCAGATCG CCACACCGAC

1151  CGACCGTATC GCAGGAGCAT TTAATGCGAG GATCGCCTGA CACCTTATCC

1201  TGACGCGCGC TCTTCAGTCG ACAGAGCCGA AGTGACCGCA ATCACTTCGC

1251  CGCTCCACTG ACCGACCTGA CAAGAAGACA GCGCCGCCTG CGTCGCTCCG

1301  ACTGCTGTGC CACTCGACAG AGTGAGGCTG ACAGCAGCCA AGTCCGGCCT

1351  CGGGCGCCAT AGGAAGCTCC GCCTCGCCCG ACCCTAGGGC TCGGACTCGG

1401  CCTCGGCTCC GGAAGACGAC GAACTACGCT TCGCCCGACC CCAGGGCTTG

1451  GACTCAGCCT CGGCTCCGGA AGACGACGAA TTCCGCCTCG CCCGACCCCA

1501  GGGCTCGGAC TCGGCCTCGG CTCCAGAAGA CGACGAACTC CGCCTCGCCC

1551  GACCCCAGGG CTCGGACTCA GCCTCGGCTC CGGAAGACGA CGAACTCCGC

1601  CTCGCCCGAC CCCAGGGCTC GGACTCAGCC TCGGCCTCAG ACGATGGTCT

1651  CCGCCTCGCC CGACCCGGGG CTCGGACTCG A

Region 4 (SEQ ID NO: 31) Fragment of cry1F gene
1682        CCTTTCTAT CGGACCTTGT

1701  CAGATCCTGT CTTCGTCCGA GGAGGCTTTG GCAATCCTCA CTATGTACTC

1751  GGTCTTAGGG GAGTGGCCTT TCAACAAACT GGTACGAATC ACACCCGCAC

1801  ATTCAGGAAC TCCGGGACCA TTGACTCTCT AGATGAGATA CCACCTCAAG

1851  ACAACAGCGG CGCACCTTGG AATGACTACT CCCATGTGCT GAATCATGTT

1901  ACCTTTGTGC GCTGGCCAGG TGAGATCTCA GGTTCCGACT CATGGAGAGC

1951  ACCAATGTTC TCTTGGACGC ATCGTAGCGC TACCCCCACA AACACCATTG

2001  ATCCAGAGAG AATCAC

Region 5 (SEQ ID NO: 32) Fragment of maize chloroplast rpoC2
gene
2017        TCAT TCTTCAAGAA CTGCATATCT TGCCGAGATC

2051  CTCATCCCTA AAGGTACTTG ACAATAGTAT TATTGGAGTC GATACACAAC

2101  TCACAAAAAA TACAAGAAGT CGACTAGGTG GATTGGTCCG AGTGAAGAGA

2151  AAAAAAAGCC ATACAGAACT CAAAATCTTT TCCGGAGATA TTCATTTTCC

2201  TGAAGAGGCG ATAAGATAT TAGGTGGCAG TTTGATACCA CCAGAAAGAG

2251  AAAAAAAAGA TTCTAAGGAA TCAAAAAAAA GGAAAAATTG GTTTATGTT

2301  CAACGGAAAA AATTTCTCAA AAGCAAGGAA AAGTATT

Region 6 (SEQ ID NO: 33) Fragment of maize chloroplast or
ubiZM1(2) promoter
2338        GTG GCTATTTATC

2351  TATC

Nucleotides 2355-2358 (CGT) connect Region 6 to Region 7a.

Region 7a (SEQ ID NO: 34) Fragment of pat gene
2358        GCA GCTGATATGG CCGCGGTTTG TGATATCGTT AACCATTACA

2401  TTGAGACGTC TACAGTGAAC TTTAGGACAG AGCCACAAAC ACCACAAGAG

2451  TGGATTGATG ATCTAGAGAG GTTGCAAGAT AGATACCCTT GGTTGGTTGC

2501  TGAGGTTGAG GGTGTTGTGG CTGGTATTGC TTACGCTGGG CCCTGGAAGG

2551  CTAGGAAC
```

-continued

```
Region 7b (SEQ ID NO: 35) Fragment of pat gene (complement)
2559    CC TCAACCTCAG CAACCAACCA ATGGTATCTA TCTTGCAACC

2601    TCTCTAGATC ATCAATCCAC TCTTGTGGTG TTTGTGGCTC TGTCCTAAAG

2651    TTCACTGTAG ACGTCTCAAT GTAATGGTTA ACGATATCAC AAACCG

Region 7c (SEQ ID NO: 36) Fragment of cry1F gene (complement)
2697    AGAG

2701    AAGAGGGATC T

Region 8 (SEQ ID NO: 37) Fragment of Polylinker
2712    CGAAGCTTC GGCCGGGGCC CATCGATATC CGCGGGCATG

2751    CCTGCAGTGC AGCGTGACCC GGTCGTGCCC CTCTCTAGAG ATAATGAGCA

2801    TTGCATGTCT AAGTTATAAA AAATTACCA

Region 9 (SEQ ID NO: 25) Full-length insert of PHI8999A
```

Example 5

Description of the Flanking Sequence 5' to the Insert in Maize Event TC1507

In order to more fully describe the event TC1507 5' flanking sequence, homology searching was done against the GenBank public databases (release 122, February 2001) using the Basic Local Alignment Search Tool (BLAST). The BLAST program performs sequence similarity searching and is particularly useful for identifying homologs to an unknown sequence. In addition to searching the public databases, pair-wise alignments were performed using AlignX (InforMax Inc., Bethesda, Md.) to look for homology between the maize event TC1507 flanking sequence and the PHI8999A transgenic insert. The results of these homology searches are presented in Table 1. The TC1507 5' flanking sequence is numbered with base 1 being the furthest 5' to the insert and base 2830 at the starting point of the full-length PHI8999A transgenic insert (see FIG. 1). The percent identity values indicate the percentage of identical matches across the length of the sequences analyzed.

In most cases, similarity searching with the event TC1507 5' flanking sequence resulted in a match to one unique sequence based on a very high percent identity value. Those sequences are identified in Table 1. In addition, there are two regions in the TC1507 5' DNA flanking sequence with high similarity to more than one known sequence. In regions 870-1681 and 2338-2354, the percent identity scores with both sequence fragments are sufficiently high that a single match (homolog) cannot be determined. The two possible homologs for each of these regions are indicated in Table 1.

Highly similar sequences were identified for all but the first 669 base pairs of sequence. Generally, the results of similarity searching indicate high homology with maize genomic sequences 5' to base 1681. The region from base 1682 to the start of the PHI8999A insert at position 2830 contains some fragments associated with the transformation event.

TABLE 1

Sequence summary for event TC1507 insert

| Region | Location in SEQ ID NO: 24 | Size bp | % Identity | Homolog | Location in homologous sequence | Description |
| --- | --- | --- | --- | --- | --- | --- |
| 1 | 1-669 | 669 | N/A[1] | N/A | N/A | No significant homology detected |
| 2 | 670-869 | 200 | 90.5 | AF123535 | 52432-52632 (complement) | Undescribed maize genomic sequence |
| 3 | 870-1681 | 812 | 89.4 | AF050439 | 1-801 | Fragment of maize Huck-1 retrotransposon 5' LTR[2] |
|   |   |   | 86.6 | AF050438 | 1-797 | Fragment of maize Huck-1 retro-transposon 3' LTR |
| 4 | 1682-2016 | 335 | 100.0 | PHI8999A | 3149-3483 | Fragment of cry1F gene |
| 5 | 2017-2337 | 321 | 100.0 | X86563 | 29429-29749 | Fragment of maize chloroplast rpoC2 gene (RNA polymerase beta-2 subunit) |
| 6 | 2338-2354 | 17 | 100.0 | X86563 | 97643-97659 | Fragment of maize chloroplast trnI gene (tRNA-Ile) |

TABLE 1-continued

Sequence summary for event TC1507 insert

| Region | Location in SEQ ID NO: 24 | Size bp | % Identity | Homolog | Location in homologous sequence | Description |
|---|---|---|---|---|---|---|
| | | | 82.4 | PHI8999A | 182-197 | Fragment of maize ubiZM1(2) promoter |
| 7a | 2358-2558 | 201 | 100.0 | PHI8999A | 5320-5475 | Fragment of pat gene |
| 7b | 2559-2696 | 138 | 99 | PHI8999A | 5336-5518 (complement) | Fragment of pat gene |
| 7c | 2697-2711 | 15 | 100.0 | PHI8999A | 2544-2558 (complement) | Fragment of cry1F gene |
| 8 | 2712-2829 | 118 | 100.0 | PHI8999A | 36-153 | Fragment of polylinker region (bases 36-80) and ubiZM1(2) promoter (bases 81-153) |
| 9 | 2830-9015 | 6186 | 100.0 | PHI8999A | 11-6196 | Full-length insert of PHI8999A |
| 10 | 9016-9565 | 550 | 100.0 | PHI8999A | 3906-4456 (complement) | Inverted ORF25 terminator |
| 11 | 9566-9693 | 128 | 100.0 | NC_001666 | 121851-121978 (complement) & 100759-100886 | Fragment of maize chloroplast rps12 rRNA (23S ribosomal RNA) |
| 12 | 9696-10087 | 392 | 99 | NC_001666 | 17091-17483 (complement) | Fragment of maize chloroplast genome |
| 13 | 10088-10275 | 188 | 99 | PHI8999A | 5333-5520 (complement) | Fragment of pat gene |
| 14 | 10278-10358 | 81 | 100 | NC_001666 | 137122-137202 (complement) | Fragment of maize chloroplast "ORF241" - hypothetical protein gene |
| 15 | 10359-10612 | 254 | N/A[1] | N/A | N/A | No significant homology detected |
| 16 | 10613-11361 | 749 | N/A[1] | N/A | N/A | No description available |

[1]N/A; not applicable
[2]LTR; long terminal repeat

Example 6

Confirmation of the Presence of Regions 1, 2, and 3 in an Unmodified Control Corn Line PCR analysis was used to determine if Regions 1, 2, and 3 (Table 1) in the 5' flanking region of Event TC1507 are present in an unmodified control corn line used for transformation to produce maize event TC1507 and thus represents a border with corn genomic DNA. Nine different PCR analyses were carried out on genomic DNA prepared from TC1507 and the unmodified control corn line Hi-II (see Armstrong (1994) *The Maize Handbook*, ed. Freeling and Walbot, Springer-Verlag, New York, pp. 663-671, for information on Hi-II) as outlined in Table 2 using the primer sequences shown in Table 3. Two reactions were designed to amplify DNA within Region 1 of the 5' flanking region from bp 25 to 324 (Reaction A—300 bp amplicon); and from bp 25 to 480 (Reaction B—456 bp amplicon). The expected amplicons were present in both the Hi-II unmodified corn line and in maize event TC1507. One PCR primer pair, Reaction C, spanned Region 2 to Region 3 of the 5' flanking region from bp 759 to 1182 (424 bp amplicon) and again produced PCR products of the expected size in both Hi-II and TC1507. Reaction D, spanned Region 1 to Region 3 of the 5' flanking region from bp 415 to 1182 (768 bp amplicon) and again produced PCR products of the expected size in both Hi-II and TC1507. Reactions E and F were designed as specific primer pairs for the pat gene region of the full-length insert of PHI8999A in TC1507 and thus an amplicon in the unmodified Hi-II corn line is not expected. The results indicate that both Reactions E and F are specific for a maize line transformed with a pat gene region and produce the expected amplicon, whereas no amplicon was produced in the unmodified Hi-II corn line. Reaction G was also designed as a primer pair that would produce an amplicon of 366 bp in the maize event TC1507 and no amplicon in the unmodified Hi-II corn line.

Reactions H and I were designed as specific primer pairs for TC1507 that would span the end of the transgenic insert into the 5' flanking region. In both Reactions H and I, the reverse primer was located in the ubiquitin promoter region of the full-length PHI8999A insert (Region 9 in Table 1) and the forward primer was located in Region 5, the rpoC2 gene fragment (see Table 1). Reaction H and Reaction I both produced an amplicon in maize line TC1507 and did not produce an amplicon in the unmodified control corn line. These results indicate that both Reactions H and I are specific for the TC1507 event.

The PCR results show that the undescribed sequence (Region 1) is present in the unmodified corn line Hi-II and that Regions 1, 2 and 3, are contiguous in the unmodified corn line Hi-II. The DNA sequences amplified in Reactions A, B, C, and D are not unique to the 5' flanking region of maize event TC1507 but are also present in the unmodified corn line Hi-II.

TABLE 2

PCR reactions for sequence 5' to the PHI8999A insert in maize event TC1507 and for regions within the full-length insert of PHI8999A in maize event TC1507

| Reaction | PCR Amplicon Location | Amplicon Size (bp) | Region in TC1507 flanking sequence or PHI8999A insert | Amplicon present In Hi-II | Amplicon present in maize line TC1507 |
|---|---|---|---|---|---|
| A | 25-324 bp in TC1507 flanking sequence | 300 | Region 1 | Yes | Yes |
| B | 25-480 bp in TC1507 flanking sequence | 456 | Region 1 | Yes | Yes |
| C | 759-1182 bp in TC1507 flanking sequence | 424 | Region 2 to Region 3 | Yes | Yes |
| D | 415-1182 bp in TC1507 5' flanking sequence | 768 | Region 1 to Region 3 | Yes | Yes |
| E Not Unique to TC1507 | 4750-5794 bp in PHI8999A | 1045 | Region 9 (in full-length insert of PHI8999A 35S promoter to pat gene) | No | Yes |
| F Not Unique to TC1507 | 4827-5308 bp in PHI8999A | 482 | Region 9 (in full-length insert of PHI8999A 35S promoter to pat gene) | No | Yes |
| G Detects cry1F fragment in 5' flanking region | cry1F sequence in 5' flanking sequence and in full-length insert of PHI8999A | 366 | Spans 335 bp cry1F sequence in 5' flanking sequence and same sequence in the full-length insert | No | Yes |
| H Unique to TC1507 | 2158 bp in Region 5 (rpoC2 gene fragment) to 3069 bp in Region 9 (full-length insert of PHI8999A) | 912 | Region 5 to Region 9 Unique to Insertion Event [SPANS UNIQUE JUNCTION REGIONS] | No | Yes |
| I Unique to TC1507 | 2158 bp in Region 5 (rpoC2 gene fragment) to 3001 bp in Region 9 (full-length insert of PHI8999A) | 844 | Region 5 to Region 9 Unique to Insertion Event [SPANS UNIQUE JUNCTION REGIONS] | No | Yes |

TABLE 3

PCR primers for sequence 5' to the PHI8999A insert in TC1507 and for regions within the full-length insert of PHI8999A in maize event TC1507

| Reaction | Amplicon Size (bp) | Primer Pair | Primer Sequences 5' to 3' |
|---|---|---|---|
| A | 300 | SEQ ID NO: 10 | CCCCTACCCCACCGACGTTTAT |
|   |     | SEQ ID NO: 11 | TTGATTGGCAGGTCCGTGGGTC |
| B | 456 | SEQ ID NO: 10 | CCCCTACCCCACCGACGTTTAT |
|   |     | SEQ ID NO: 12 | CACAACGGCACAGAAACACGAA |

TABLE 3-continued

PCR primers for sequence 5' to the PHI8999A insert in
TC1507 and for regions within the full-length insert of
PHI8999A in maize event TC1507

| Reaction | Amplicon Size (bp) | Primer Pair | Primer Sequences 5' to 3' |
|---|---|---|---|
| C | 424 | SEQ ID NO: 13 | GCGCACCCACCGGAACAAAATG |
|   |     | SEQ ID NO: 14 | TCCTCGCATTAAATGCTCCTGC |
| D | 768 | SEQ ID NO: 15 | CCTGGCACGCATTGACGCATGT |
|   |     | SEQ ID NO: 14 | TCCTCGCATTAAATGCTCCTGC |
| E | 1045 | SEQ ID NO: 6 | TAGAGGACCTAACAGAACTCGCCGT |
|   |      | SEQ ID NO: 7 | GAGCTGGCAACTCAAAATCCCTTT |
| F | 482 | SEQ ID NO: 8 | AAAATCTTCGTCAACATGGTGGAGC |
|   |     | SEQ ID NO: 9 | TAATCTCAACTGGTCTCCTCTCCGG |
| G | 366 | SEQ ID NO: 19 | GGCTCGGACTCGACCTTTCTAT |
|   |     | SEQ ID NO: 20 | GCAGTTCTTGAAGAATGAGTGA |
| H | 912 | SEQ ID NO: 1 | GTAGTACTATAGATTATATTATTCGTAGAG |
|   |     | SEQ ID NO: 2 | GCCATACAGAACTCAAAATCTTTTCCGGAG |
| I | 844 | SEQ ID NO: 2 | GCCATACAGAACTCAAAATCTTTTCCGGAG |
|   |     | SEQ ID NO: 23 | CTTCAAACAAGTGTGACAAA |

Example 7

Flanking Sequence 3' to Inserted Transgenic DNA in Maize Event TC1507

Two separate PCR approaches were used to extend the length of the sequence information 3' to the full-length PHI8999A insert in maize event TC1507. In the first approach PCR primer pairs were designed to amplify a product that spanned the junction between the full-length insert and the inverted ORF25 terminator, see FIG. 1 for a depiction of the inverted ORF25 terminator. A forward primer was located at the end of the full-length PHI8999A insert and a series of reverse primers were located at 100 bp intervals in the inverted sequence. In this manner the length of the inverted fragment present in the maize event TC1507 could be determined within a 100 bp region based on the successful PCR reactions. This method indicated the inverted fragment contained the majority of the ORF25 terminator but no Cry1F sequence. PCR fragments were isolated and sequenced from this region.

In the second approach PCR primers were designed to walk out into the flanking DNA sequence from the inverted ORF25 terminator region as determined in the PCR experiment described above. Genomic DNA isolated from two to three individual plants of event TC1507 and an unmodified control corn line was digested with various restriction enzymes and then ligated to adaptors specific for the restriction enzyme used for digestion (Universal Genome Walker™ Kit, Clontech Laboratories, Inc. and Devon et al. (1995) *Nucleic Acids Res.* 23:1644-1645). Primary PCR was carried out using an ORF25 terminator specific primer and a primer homologous to the adaptor sequence ligated onto the digested DNA. In order to increase the specificity of the reaction a nested secondary PCR was performed again with another ORF25 terminator specific primer and a secondary primer homologous to the adaptor sequence with the secondary primers being internal to the respective primers used in the primary PCR. Products produced by the nested PCR were analyzed by agarose gel electrophoresis and fragments unique to TC1507 DNA samples were isolated and sequenced. Fragments were amplified from both the ORF25 terminator contained within the full-length insert and from the targeted (inverted) ORF25 terminator on the 3' end of the full-length PHI8999A insert. Fragments from the full-length insert were of a predicted size based on the knowledge of the restriction enzyme sites located in the full-length insert. Fragments produced from the 3' inverted ORF25 terminator appeared as fragments of unexpected size. Sequence analysis of amplified fragments from the 3' inverted ORF25 terminator resulted in flanking DNA sequence of 1043 bp. Resultant sequence from the above series of genome walking experiments was used to design additional primers to walk further out from the insert into the bordering maize genome with a final 3' flanking sequence, of 2346 bp.

In order to describe the TC1507 3' flanking sequence, homology searching was done against the GenBank public databases using the Basic Local Alignment Search Tool (BLAST). The BLAST program performs sequence similarity searching and is particularly useful for identifying homologs to an unknown sequence. In addition to searching the public databases, alignments were performed using Seq-Man 4.05™, Martinez and Needleman-Wunsch alignment algorithms (DNASTAR Inc.) to look for homology between the TC1507 3' flanking sequence and the PHI8999A transgenic insert. The results of these homology searches are presented in Table 1. The percent identity values indicate the percentage of identical matches across the length of the sequences analyzed. The results of similarity searching for the 3' flanking sequence indicate high homology with three regions of maize chloroplast DNA, a 188 bp fragment of the pat gene, and 254 bp of DNA (Region 15, Table 1) with no significant homology. An additional 749 bp (Region 16) beyond Region 15 (see Table 1) was also sequenced. No similarity searching results are available for Region 16.

PCR analysis on control and TC1507 genomic DNA determined that the 254 bp sequence (Region 15, fragment of maize chloroplast "ORF241") is present in the maize genome. The DNA sequence of Region 15 in the 3' flanking region is not unique to the 3' flanking region of maize event TC1507 but is also present in the unmodified control corn line. The TC1507 3' flanking sequence is presented in Example 8 and diagrammed in FIG. 1.

Example 8

Sequence of the Region 3' to the End of the
Full-Length Insert DNA in Maize Event TC1507. A
Description of Each Region is in Table 1

```
Region 10 (SEQ ID NO: 38) Fragment of ORF25 Terminator
(complement)
 9016  CTCAC TCCGCTTGAT CTTGGCAAAG ATATTTGACG

9051  CATTTATTAG TATGTGTTAA TTTTCATTTG CAGTGCAGTA TTTTCTATTC

9101  GATCTTTATG TAATTCGTTA CAATTAATAA ATATTCAAAT CAGATTATTG

9151  ACTGTCATTT GTATCAAATC GTGTTTAATG GATATTTTTA TTATAATATT

9201  GATGATATCT CAATCAAAAC GTAGATAATA ATAATATTTA TTTAATATTT

9251  TTGCGTCGCA CAGTGAAAAT CTATATGAGA TTACAAAATA CCGACAACAT

9301  TATTTAAGAA ACATAGACAT TAACCCTGAG ACTGTTGGAC ATCAACGGGT

9351  AGATTCCTTC ATGCATAGCA CCTCATTCTT GGGGACAAAA GCACGGTTTG

9401  GCCGTTCCAT TGCTGCACGA ACGAGCTTTG CTATATCCTC GGGTTGGATC

9451  ATCTCATCAG GTCCAATCAA ATTTGTCCAA GAACTCATGT TAGTCGCAAC

9501  GAAACCGGGG CATATGTCGG GTATCTCGAG CTCGCGAAAG CTTGGCTGCA

9551  GGTCGACGGA TCCTT

Region 11 (SEQ ID NO: 39) Fragment of maize chloroplast
rps12 rRNA gene (complement)
 9566  CAACA AAAGGGTACC TGTACCCGAA ACCGACACAG

9601  GTGGGTAGGT AGAGAATACC TAGGGGCGCG AGACAACTCT CTCTAAGGAA

9651  CTCGGCAAAA TAGCCCCGTA ACTTCGGGAG AAGGGGTGCC CCC

Nucleotides 9694-9695 (CG) connect Region 11 to Region 12.

Region 12 (SEQ ID NO: 40) Fragment of maize chloroplast
genome
 9696  CTAAC

9701  AATAAACGAA TACGGTTTAT GTATGGATTC CGGTAAAATA CCGGTACTCG

9751  ATTTCATAAG AGTCGAATAG GAAGTTAAGA TGAGGGTGGT ATCATCATAA

9801  AAATGGAGTA GTATCCTAAA TTATACTAAT CCACGTATGA TATGTATGCC

9851  TTTCCTTATC AACCGGAAGT AGTGCAAAAA AAATTCTATA CTGCACTGCT

9901  CTCTTTTTAC TGAGAAATGC AAAAAAATAA AAGTGAAGTA AGGGTGCCCC

9951  ATAGATATTT GATCTTGCCT CCTGTCCCCC CCCCCCTTTT TTCATCAAAA

10001  ATTTCCATGA AAAAGAAAA GATGAATTTG TCCATTCATT GAACCCTAGT

10051  TCGGGACTGA CGGGGCTCGA ACCCGCAGCT TCCGCCT

Region 13 (SEQ ID NO: 41) Fragment of pat gene (complement)
10088  GTT CCTAGCCTTC

10101  CAGGGCCCAG CGTAAGCAAT ACCAGCCACA GCACCCTCAA CCTCAGCAAC

10151  CAACCAAGGG TATCTATCTT GCAACCTCTC TAGATCATCA ATCCACTCTT

10201  GTGGTGTTTG TGGCTCTGTC CTAAAGTTCA CTGTAGACGT CTCAATGTAA

10251  TGGTTAACGA TATCACAAAC CGCGG

Nucleotides 10276-10277 (AA) connect Region 13 to Region 14.

Region 14 (SEQ ID NO: 42) Fragment of maize chloroplast
ORF241 (complement)
10278  CAC AAGAACGAAA GCACCTTTTC
```

```
                                    -continued
10301  ATTCTTTCAT ATACTAGGGG TTTTTACTTG GAAAAGACAA TGTTCCATAC

10351  TAAAGGAT

Region 15 (SEQ ID NO: 43) Maize genomic (no significant
homology)
10359     AG CTGCAGAAGC CGCCACCGTC TTGAGGACCT TCCGGGGAGC

10401  CAGACCGGTC GAACCGTGCC TCCACTTGCT AAGGAGAAAG
       GGAAAATCAG

10451  GGCCAGGACA TACGAAGGAG GAGCCAGAAC GAAGATATCC
       TAAGATACTT

10501  ACTCGCTCCG GGCCATGATC AATCATGCCT GTGGGGAGGT CTCTCGCACC

10551  TCGATCCATG AAGGTACCAC CGAGGTCTGC CCCGCCGCCG GCTTCGGTAC

10601  CGTCCTCGCC TT

Region 16 (SEQ ID NO: 44) Maize genomic
10613  GGGCGCCC GAGGCACCCG GGGGATGGAC TGCCCAGGCG

10651  CAGCCACGAC GACCCAAGGA TCACCCTCCT GCGCAGTCGG
       CACGAGCAAT

10701  AGTTCTCGGG GAACAGGCAG CTTGGCCTGA CTCCCCGGGG TCACCTCAAC

10751  TACCTCGGCC GAGGGGTCAA GTACCCCCTC AGTCCGCCCC CGCTCTTCGG

10801  ACCGGGACCC CGACGTCCCG GCCCCGGATA CCGACGGCAC CAGCCCGCTC

10851  GGGGGCTGGC TTGACGACCC CTGGCCCAGC CTCAGATCTG GGCTGAGGCC

10901  GAGGCAGGCG GCCATGTCGT CGTCTTCATC ATCGTCTTCA TCATCGTCGT

10951  CGTCATCAGG CGTCTCCGGC GACGGCTCCC TTGGGAGCCC CTCCCTCTCC

11001  TGCCGACGAC GAAGCCTTTC CAAGGCATCC CGAGCCCACG TCCGCTCGTG

11051  GGCCCGAGCC TTCTTTGCGT CCTTCTTCTC CTTCCTCTTC TCCGCGGTGA

11101  CCCTCCGCGC AGCTCGGTCC ACCGCATCCT CCGGGACTGG TGGCAGGGAA

11151  GGCTTGTGAT GCCCTACCTC CTGGAGACAG ACGAAAAGTC TCAGCTATGA

11201  GAACCGAGGG CAATCTGACG CAAGAAGGAA GAAGGAGCGG ATACTCACCA

11251  GAGACACGCA CCCGCGATCG GGACGCATTA AGGGCTGGGA AAAAGTGCCG

11301  GCCTCTAATT TCGCTACCGT GCCGTCCACC CACCTGTGGA GGTCATCGAT

11351  GGGAAGGGGA A
```

Example 9

Confirmation of the Presence of Region 15 in the Unmodified Control Corn Line PCR analysis was used to determine if the undescribed region of sequence on the end of the 3' flanking sequence (Region 15 in Table 1) is present in the unmodified control corn line used for transformation to produce maize event TC1507 and thus represents a border with corn genomic DNA. Successful PCR amplification of Region 15 in both maize line TC1507 and the unmodified Hi-II control corn line revealed that Region 15 was indeed present in corn genomic DNA. Five different PCR analyses were carried out on genomic DNA prepared from TC1507 and the unmodified Hi-II control corn line as outlined in Table 7 below using the primer sequences shown in Table 8. Three reactions were designed to amplify DNA within Region 15 of the 3' flanking region; Reaction L—producing a 175 bp amplicon, Reaction M—producing a 134 bp amplicon, and Reaction N—producing a 107 bp amplicon. The expected amplicons were present in both the unmodified control corn line and in maize line TC1507. Reactions J and K were designed as specific primer pairs for TC1507 that would span the end of the insert into the 3' flanking region. In Reaction J, the forward primer was located in the pat gene fragment on the 3' end of the full-length PHI8999A insert (Region 13 in Table 1) and the reverse primer was located in the undefined Region 15. In Reaction K the forward primer was located in the chloroplast hypothetical protein gene on the 3' end of the full-length insert (Region 14 in Table 1) and the reverse primer was located in the undefined Region 15. Both Reaction J and Reaction K produced an amplicon in maize line TC1507 and did not produce an amplicon in the unmodified control corn line. The results indicate that both Reactions J and K are specific for the TC1507 event.

The PCR results indicate that the undescribed sequence (Region 15) of the 3' flanking sequence of TC1507 is also present in genomic DNA isolated from the unmodified Hi-II control corn line. The DNA sequences amplified in Reactions L, M, and N are not unique to the 3' flanking region of TC1507 but are also present in the unmodified control corn line.

TABLE 7

PCR reactions for sequence 3' to the PHI8999A insert in maize event TC1507

| Reaction | Amplicon Size (bp) | Region in TC1507 3' flanking sequence | Amplicon present in Control | Amplicon present in maize line TC1507 |
|---|---|---|---|---|
| J | 342 | Region 13 (pat gene fragment) to Region 15 | No | Yes |
| K | 252 | Region 14 (chloroplast gene) to Region 15 | No | Yes |
| L | 175 | Region 15 | Yes | Yes |
| M | 134 | Region 15 | Yes | Yes |
| N | 107 | Region 15 | Yes | Yes |

TABLE 8

PCR primers for sequence 3' to the PHI8999A insert in maize event TC1507

| Reaction | Amplicon Size (bp) | Primer Pair | Primer Sequences 5' to 3' |
|---|---|---|---|
| J | 342 | SEQ ID NO: 3 | TGTGGTGTTTGTGGCTCTGTCCTAA |
|   |   | SEQ ID NO: 5 | GACCTCCCCACAGGCATGATTGATC |
| K | 252 | SEQ ID NO: 4 | AGCACCTTTTCATTCTTTCATATAC |
|   |   | SEQ ID NO: 5 | GACCTCCCCACAGGCATGATTGATC |
| L | 175 | SEQ ID NO: 16 | AAGCCGCCACCGTCTTGAGGACCTT |
|   |   | SEQ ID NO: 5 | GACCTCCCCACAGGCATGATTGATC |
| M | 134 | SEQ ID NO: 17 | GTCGAACCGTGCCTCCACTTGCTAA |
|   |   | SEQ ID NO: 5 | GACCTCCCCACAGGCATGATTGATC |
| N | 107 | SEQ ID NO: 18 | AGAAAGGGAAAATCAGGGCCAGGAC |
|   |   | SEQ ID NO: 5 | GACCTCCCCACAGGCATGATTGATC |

Example 10

PCR Primers

DNA event specific primer pairs were used to produce an amplicon diagnostic for TC1507. These event primer pairs include, but are not limited to, SEQ ID NO: 1 and SEQ ID NO: 2; SEQ ID NO: 2 and SEQ ID NO: 23; SEQ ID NO: 3 and SEQ ID NO: 5; and SEQ ID NO: 4 and SEQ ID NO: 5. In addition to these primer pairs, any primer pair derived from SEQ ID NO: 26 and SEQ ID NO: 27 that when used in a DNA amplification reaction produces a DNA amplicon diagnostic for TC1507 is an aspect of the present invention. The amplification conditions for this analysis are illustrated in Table 9, however, any modification of these methods that use DNA primers or complements thereof to produce an amplicon DNA molecule diagnostic for TC1507 is within the ordinary skill of the art. The preferred amplification conditions for reactions utilizing the PCR primers identified in SEQ ID NOS: 1, 2, and 23 are illustrated in Table 10. In addition, control primer pairs, which include SEQ ID NOS: 10 and 11; SEQ ID NOS: 10 and 12; SEQ ID NOS: 13 and 14; SEQ ID NOS: 14 and 15; SEQ ID NOS: 5 and 16; SEQ ID NOS: 5 and 17; and SEQ ID NOS: 5 and 18; for amplification of an endogenous corn gene are included as internal standards for the reaction conditions. Also included are primer pairs that will produce an amplicon in transgenic events containing a pat gene (SEQ ID NOS: 6 and 7; SEQ ID NOS: 8 and 9), and a primer pair that will produce an amplicon in transgenic events containing a cry1F gene (SEQ ID NOS: 19 and 20).

The analysis of plant tissue DNA extracts to test for the presence of the TC1507 event should include a positive tissue DNA extract control (a DNA sample known to contain the transgenic sequences). A successful amplification of the positive control demonstrates that the PCR was run under conditions which allow for the amplification of target sequences. A negative, or wild-type, DNA extract control in which the template DNA provided is either genomic DNA prepared from a non-transgenic plant, or is a non-TC1507 transgenic plant, should also be included. Additionally a negative control that contains no template corn DNA extract will be a useful gauge of the reagents and conditions used in the PCR protocol.

Additional DNA primer molecules of sufficient length can be selected from SEQ ID NO: 26 and SEQ ID NO: 27 by those skilled in the art of DNA amplification methods, and conditions optimized for the production of an amplicon that may differ from the methods shown in Table 9 or Table 10 but result in an amplicon diagnostic for event TC1507. The use of these DNA primer sequences with modifications to the methods shown in Table 9 and Table 10 are within the scope of the invention. The amplicon wherein at least one DNA primer molecule of sufficient length derived from SEQ ID NO: 26 and SEQ ID NO: 27 that is diagnostic for event TC1507 is an aspect of the invention. The amplicon wherein at least one DNA primer of sufficient length derived from any of the genetic elements of PHI8999A that is diagnostic for event TC1507 is an aspect of the invention. The assay for the TC1507 amplicon can be performed by using a Stratagene Robocycler, MJ Engine, Perkin-Elmer 9700, or Eppendorf Mastercycler Gradient thermocycler, or by methods and apparatus known to those skilled in the art.

TABLE 9

PCR Conditions:

| Conditions: | |
|---|---|
| Kit used: | Perkin-Elmer AmpliTAQ Gold kit |
| Volume | Component |
| 5 µl | template (10 ng/µl) |
| 4 µl | 2 µl each primer (10 µM) |
| 2 µl | 10X PCR Gold Buffer |

TABLE 9-continued

PCR Conditions:

| | |
|---|---|
| 2 µl | 25 mM MgCl$_2$ |
| 2 µl | 50X dNTP's (10 mM) |
| 0.1 µl | Amplitaq Gold Polymerase |
| 4.9 µl | H$_2$O |
| 20 µl | Total |

Cycling Parameters

GeneAmp ® PCR System 9700
9 min 92° C.
30 cycles:

94° C. 30 sec
60° C. 30 sec
72° C. 1 min
7 min 72° C.
Hold 4° C.

TABLE 10

PCR Conditions used with the Advantage ®-GC 2 Polymerase Mix:

Conditions:

| Kit used: | Advantage ®-GC 2 Polymerase Mix |
|---|---|
| Volume | Component |
| 5 µl | template (10 ng/µl) |
| 5 µl | 2.5 µl each primer (10 µM) |
| 10 µl | 5x GC2 Buffer |
| 10 µl | GC melt (1.0 M final conc.) |
| 1.5 µl | 50X dNTP's (10 mM) |
| 1.0 µl | Advantage GC2 Polymerase |
| 17.5 µl | H$_2$O |
| 50 µl | Total |

Cycling Parameters

GeneAmp ® PCR System 9700
5 min 94° C.
35 cycles:

94° C. 1 min
60° C. 2 min
72° C. 3 min
7 min 72° C.
Hold 4° C.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A DNA detection kit comprising a primer pair, wherein said primer pair is capable of producing in a thermal amplification reaction an amplicon diagnostic for the presence of DNA corresponding to corn event TC 1507, wherein said primer pair consists of a first polynucleotide primer and a second polynucleotide primer, and wherein said first and second primers are selected from the group consisting of:

(a) a primer consisting of at least 11 contiguous nucleotides selected from the maize sequence set forth in nucleotides 1-1001 of SEQ ID NO: 27 or its full complement;

(b) a primer consisting of at least 11 contiguous nucleotides selected from the maize DNA sequence set forth in nucleotides 1002-1551 of SEQ ID NO: 27 or its full complement;

(c) a primer consisting of at least 11 contiguous nucleotides selected from the maize DNA sequence set forth in nucleotides 1552-1679 of SEQ ID NO: 27 or its full complement;

(d) a primer consisting of at least 11 contiguous nucleotides selected form the maize DNA sequence set forth in nucleotides 1682-2073 of SEQ ID NO: 27 or its full complement;

(e) a primer consisting of at least 11 contiguous nucleotides selected from the maize DNA sequence set forth in nucleotides 2074-2261 of SEQ ID NO: 27 or its full complement;

(f) a primer consisting of at least 11 contiguous nucleotides selected from the maize DNA sequence set forth in nucleotides 2264-2344 of SEQ ID NO: 27 or its full complement; and (g) a primer consisting of at least 11 contiguous nucleotide selected from the maize DNA sequence set forth in nucleotides 2345-2598 of SEQ ID NO: 27 or its full complement;

wherein the amplicon produced in the thermal amplification reaction comprises at least 20 contiguous nucleotides spanning at least one of the junction regions unique to corn event TC1507 selected from the group consisting of:

(l) nucleotides 992-1011 of SEQ ID NO: 27;
(m) nucleotides 1542-1561 of SEQ ID NO: 27;
(n) nucleotides 1671-1690 of SEQ ID NO: 27;
(o) nucleotides 2064-2083 of SEQ ID NO: 27;
(p) nucleotides 2253-2272 of SEQ ID NO: 27; and
(q) nucleotides 2335-2344 of SEQ ID NO: 27.

* * * * *